(12) United States Patent
Breton et al.

(10) Patent No.: US 10,169,544 B2
(45) Date of Patent: Jan. 1, 2019

(54) SIMULATION OF ENDOGENOUS AND EXOGENOUS GLUCOSE/INSULIN/GLUCAGON INTERPLAY IN TYPE 1 DIABETIC PATIENTS

(71) Applicant: University of Virginia Patent Foundation, Charlottesville, VA (US)

(72) Inventors: Marc D. Breton, Charlottesville, VA (US); Boris P. Kovatchev, Charlottesville, VA (US); Chiara Dalla Man, Venice (IT); Claudio Cobelli, Padua (IT); Francesco Micheletto, Padua (IT)

(73) Assignee: University of Virginia Patent Foundation, Charlottesville, VA (US)

( * ) Notice: Subject to any disclaimer, the term of this patent is extended or adjusted under 35 U.S.C. 154(b) by 282 days.

(21) Appl. No.: 14/902,731

(22) PCT Filed: Jul. 3, 2014

(86) PCT No.: PCT/US2014/045393
§ 371 (c)(1),
(2) Date: Jan. 4, 2016

(87) PCT Pub. No.: WO2015/003124
PCT Pub. Date: Jan. 8, 2015

(65) Prior Publication Data
US 2016/0171183 A1    Jun. 16, 2016

Related U.S. Application Data

(60) Provisional application No. 61/842,789, filed on Jul. 3, 2013.

(51) Int. Cl.
*G06F 19/00* (2018.01)
*G16H 50/50* (2018.01)

(52) U.S. Cl.
CPC ............ *G06F 19/702* (2013.01); *G06F 19/00* (2013.01); *G16H 50/50* (2018.01)

(58) Field of Classification Search
CPC .......... A61M 5/1723; A61M 2230/201; A61B 5/4839; A61B 5/14532; G06F 19/3468; G06F 19/3437
(Continued)

(56) References Cited

U.S. PATENT DOCUMENTS

| 2010/0179768 A1* | 7/2010 | Kovatchev | .......... | G06F 19/3437 |
| | | | | 702/19 |
| 2012/0059353 A1* | 3/2012 | Kovatchev | .......... | G06F 19/3437 |
| | | | | 604/504 |

(Continued)

FOREIGN PATENT DOCUMENTS

| WO | 2010151834 A1 | 12/2010 |
| WO | 2012178134 A2 | 12/2012 |

OTHER PUBLICATIONS

Makroglou et al. "Mathematical models and software tools for the glucose-insulin regulatory system and diabetes: an overview"; Applied Numerical Mathematics 56 (2006), pp. 559-573.

*Primary Examiner* — Changhyun Yi
(74) *Attorney, Agent, or Firm* — Vorys, Sater, Seymour and Pease LLP; Vincent M DeLuca; Robert J. Decker

(57) ABSTRACT

A simulator for in-silico testing of Type 1 diabetes patients uses a model that puts in relation plasma concentrations, i.e., glucose G and insulin /, with glucose fluxes, i.e. endogenous glucose production (EGP), glucose rate of appearance (Ra), glucose utilization by the tissues (U), renal extraction (E), and insulin fluxes, i.e., rate of insulin appearance from the subcutaneous tissues (SC) and insulin degradation (D). A module is also included to describe counter-regulation, i.e. glucagon kinetics, secretion and action. A glucagon subcu-
(Continued)

taneous absorption model enables simulation of dual hormone control.

16 Claims, 11 Drawing Sheets

(58) Field of Classification Search
USPC .......................................................... 703/11
See application file for complete search history.

(56) References Cited

U.S. PATENT DOCUMENTS

| | | | |
|---|---|---|---|
| 2012/0130698 A1* | 5/2012 | Kovatchev | G06F 19/3437 703/11 |
| 2014/0276554 A1* | 9/2014 | Finan | A61M 5/1723 604/504 |

* cited by examiner

SIMULATION OF ENDOGENOUS AND EXOGENOUS GLUCOSE/INSULIN/GLUCAGON INTERPLAY IN TYPE 1 DIABETIC PATIENTS

CROSS-REFERENCE TO RELATED APPLICATIONS AND CLAIM OF PRIORITY

This application claims priority under 35 U.S.C. § 119(e) and PCT Article 8, of U.S. Application Ser. No. 61/842,789, filed 3 Jul. 2013. This application is also related to PCT International Application No. PCT/US2008/067725 entitled "Method, System and Computer Simulation Environment for Testing of Monitoring and Control Strategies in Diabetes," filed 20 Jun. 2008, U.S. patent application Ser. No. 12/664,444 entitled "Method, System and Computer Simulation Environment for Testing of Monitoring and Control Strategies in Diabetes," filed 14 Dec. 2009, and U.S. patent application Ser. No. 13/380,839 entitled "System, Method and Computer Simulation Environment for In Silico Trials in Pre-Diabetes and Type 2 Diabetes," filed 10 Feb. 2012, the disclosures of which are incorporated by reference herein in their entirety.

BACKGROUND OF THE INVENTION

The rapid development of the artificial pancreas in the last few years had benefit from employing mathematical modeling and computer simulation. As a matter of fact, such in-silico testing provided direction for clinical studies, out-ruling ineffective control scenarios in a cost-effective manner [1-4]. In 2008, the present Applicant introduced a computer simulator of type 1 diabetes (T1DM) based on a meal simulation model of glucose-insulin system [5-7]. This simulator was equipped with 100 in-silico adults, 100 adolescents, and 100 children, and was accepted by the FDA as a substitute for preclinical trials of certain insulin treatments, including closed-loop algorithms [8].

The FDA Accepted Simulator

The Model

The model incorporated into the T1DM simulator, which describes the glucose-insulin control system during a meal, is described in detail in [5-7]. Briefly, the model puts in relation plasma concentrations, i.e., glucose G and insulin I, with glucose fluxes, i.e. endogenous glucose production (EGP), glucose rate of appearance (Ra), glucose utilization by the tissues (U), renal extraction (E), and insulin fluxes, i.e., rate of insulin appearance from the subcutaneous tissues (SC) and insulin degradation (D). The glucose subsystem consists of a two-compartment model of glucose kinetics: insulin-independent utilization occurs in first compartment, representing plasma and rapidly equilibrating tissues, while insulin-dependent utilization occurs in the second compartment, representing peripheral slowly equilibrating tissues. The insulin subsystem is also described with two compartments, representing liver and plasma, respectively. Subcutaneous insulin kinetics is represented by a subcutaneous insulin infusion module. Endogenous glucose production is assumed to be linearly dependent on plasma glucose concentration, portal insulin concentration and a delayed insulin signal. Glucose rate of appearance is described with a model of glucose transit through the stomach and intestine, with the stomach represented by two compartments, while a single compartment is used to describe the gut; the rate constant of gastric emptying is a nonlinear function of the amount of glucose in the stomach. Glucose utilization during a meal is made up of two compartments. The insulin-independent utilization by the brain and the erythrocytes takes place in the first compartment and is constant. The insulin-dependent utilization takes place in a remote compartment and depends nonlinearly from glucose in the tissues.

The Population of Type 1 Diabetic Virtual Subjects

The type 1 diabetes simulator is equipped with 100 virtual adults, 100 adolescents and 100 children. These populations of type 1 diabetic virtual subjects have been generated by randomly extracting different realizations of the parameter vector from appropriate joint parameter distributions. The initial (2007) parameters' joint distributions in T1DM were derived (after appropriate adjustment) from the available set in the adult healthy state. In particular, the inter-subject variability was assumed to be the same (same covariance matrix), but certain clinically-relevant modifications were introduced in the average parameter vector, for instance basal endogenous glucose production is higher in type 1 diabetic compared to normal subject. Similarly, parameter distribution in different type 1 diabetic populations, such as children and adolescents, have been obtained from that of type 1 diabetic adults by introducing certain clinically-relevant modifications in the average parameter vector, for instance insulin sensitivity is higher in children and lower in adolescents compared to adults [10].

As reported in [10], the validity of the computer simulation environment was tested on independent data. Several experiments aiming to assess its capability to reflect the variety of clinical situations as close as possible were conducted. For instance we reproduced the distribution of insulin correction factors in the T1DM population of children and adults; we reproduced glucose traces in children with T1DM observed in clinical trials performed by the DirectNet consortium and glucose traces of induced moderate hypoglycemia observed in adults in clinical trials at the University of Virginia, which guarantees comprehensive evaluation of control algorithms during hypoglycemia.

Despite the good agreement between simulation and real data, the FDA accepted simulator was never validated against specific meal test data performed in type 1 diabetes. Now that these data have finally become available [1-3], the clinical validity of the simulator can be assessed against a real T1DM population observed in clinical trials simulating normal life conditions, i.e. including a meal perturbation.

In particular, recent results show that the FDA accepted simulator performs well in eu- and hyper-glycemic zones, but it fails in some occasions in describing hypoglycemic events [11], as shown in FIG. 1. Thus, there exists a need in the art to address this failure.

SUMMARY OF THE INVENTION

A modification of glucose dynamics in hypoglycemia is provided in an updated simulator based on assessment of insulin action during hypoglycemia measured in human clinical trial [23]. This required also the addition of a module describing counter-regulation, i.e. glucagon kinetics, secretion and action, which was missing in the previous release of the simulator. Finally, glucagon subcutaneous absorption was added to enable simulation of dual hormone control. Some aspects of various embodiments of the present invention provide, among other things, the following:

Glucagon subcutaneous transport to plasma
    Glucagon endogenous secretion
    Glucagon action on glucose plasma balance
    Glucose uptake in hypoglycemia
    Age of onset of diabetes for in-silico patients Here we report the equations describing insulin-dependent utilization, $U_{id}(t)$, incorporated into the T1DM simulator, for sake of comparison with the new model proposed in the following section:

$$U_{id}(t) = \frac{[V_{m0} + V_{mx} \cdot X(t)]G_t(t)}{K_{m0} + G_t(t)} \quad (1)$$

$$\dot{X}(t) = -p_{2U} \cdot X(t) + p_{2U} \cdot [I(t) - I_b] \quad X(0) = 0 \quad (2)$$

where $G_t(t)$ is the amount of glucose in the tissue, $X(t)$ is insulin action on glucose utilization and $[V_{m0}, V_{mx}, K_{m0}, p_{2U}]$ are model parameters. A complete list of model parameters and equations is reported in the Appendix A1 and A2.

Finally, new rules for determining insulin to carbohydrate ratio and correction factor of the virtual patients are implemented to better comply with physician definitions. The modifications of the simulator are described in detail in the following sections.

DETAILED DESCRIPTION OF THE INVENTION

Figure 1:
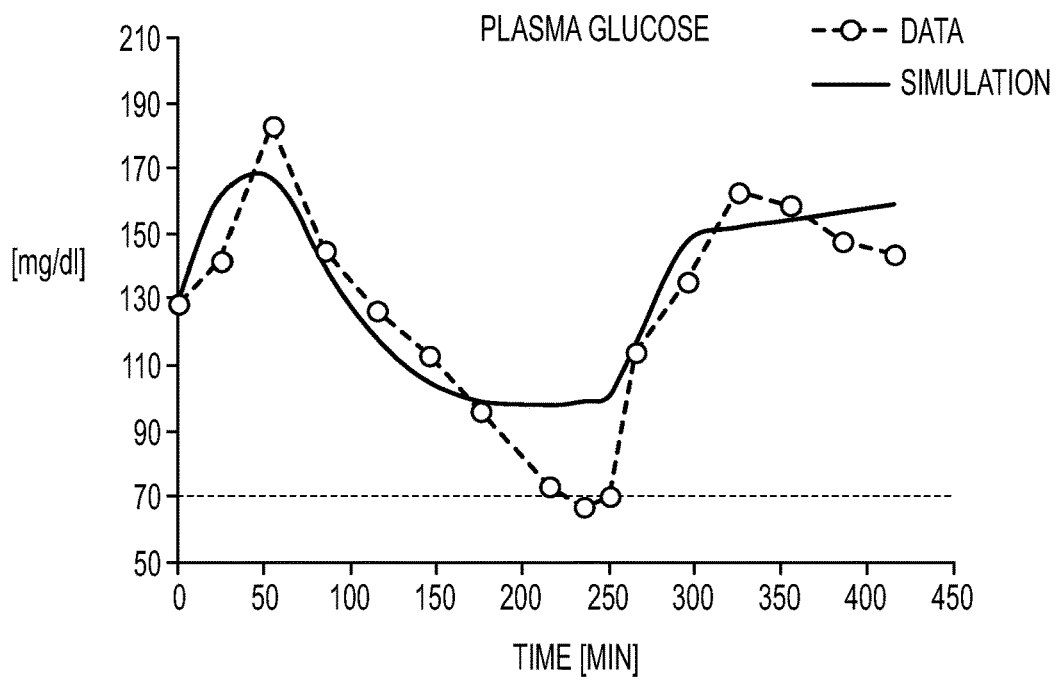
FIG. 1 is a plot showing real data versus simulations obtained with the FDA accepted simulator.
Figure 2:
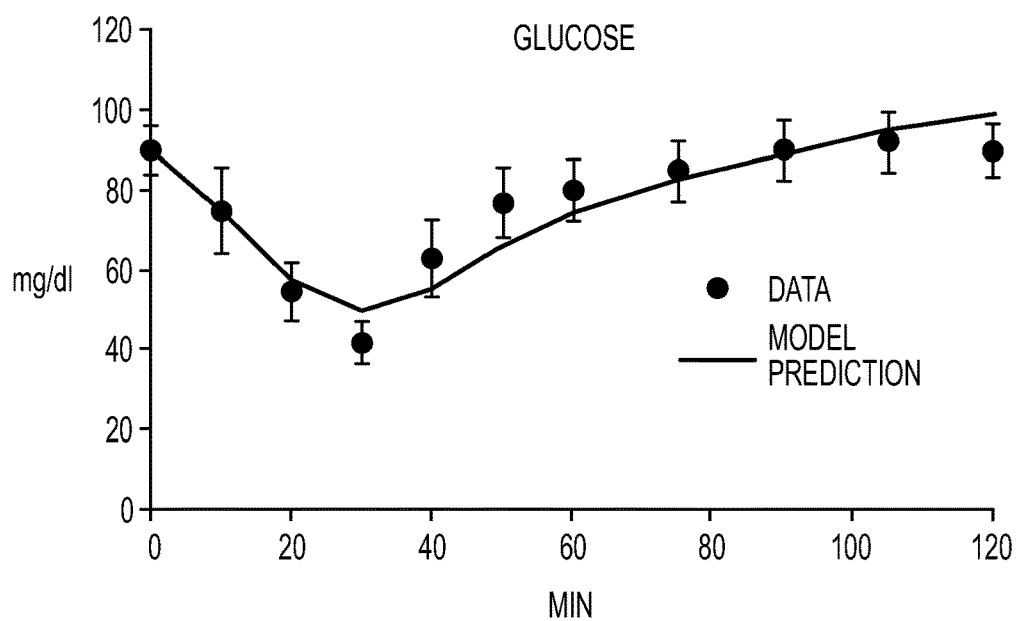
FIG. 2 is a graph showing average model prediction versus average plasma glucose concentration in 13 healthy subjects.

1) Nonlinear Response to Hypoglycemia
A) The Model
The assumption is that the insulin-dependent utilization $U_{id}(t)$ increases, when glucose decreases below a certain threshold, as the Low Blood Glucose Risk factor [12]:

$$U_{id}(t) = \frac{[V_{m0} + V_{mx} \cdot X(t) \cdot (1 + r_1 \cdot \text{risk})]G_t(t)}{K_{m0} + G_t(t)} \quad (3)$$

where $G_t(t)$, $X(t)$ and $[V_{m0}, V_{mx}, K_{m0}]$ are the same as described previously, and $$\text{risk} = \begin{cases} 0 & \text{if } G \geq G_b \\ 10 \cdot [f(G)]^2 & \text{if } G_{th} \leq G < G_b \\ 10 \cdot [f(G_{th})]^2 & \text{if } G < G_{th} \end{cases} \quad (4)$$

with $G_b$ being patient basal glucose, $G_{th}$ the hypoglycemic threshold (set at 60 mg/dl), $$f(G) = \log\left(\frac{G}{G_b}\right)^{r_2} \quad (5)$$

and [r1, r2] additional model parameters to be randomly generated.
B) Model Assessment
The model has been assessed first against data of 13 healthy subjects (8 women, 5 men; age range from 19 to 47 years; body weight within 10% of their ideal body weight). In each of them, plasma glucose recovery from insulin-induced hypoglycemia (achieved with administration of insulin 0.04 U/kg, i.v.) along with isotopically determined rate of glucose appearance (endogenous glucose production, EGP) and the circulating concentrations of glucagon, was determined [13,14]. Model prediction against data is shown in FIG. 2.

The nonlinear response to hypoglycaemia was also assessed in 32 T1DM (age 38±12 years; height 174±10 cm; weight 78±12 kg), which underwent a hyper-insulinemic euglycemic and hypoglycemic clamp, where hypoglycemia is induced at a descending rate of 1 mg/dl/min till 50 mg/dl glucose value is reached [15].

Since, in this case glucose tracers were not available, it was not possible to segregate endogenous glucose production from glucose utilization. Thus, nonlinear response to hypoglycaemia was incorporated into the glucose minimal model [16], i.e. it was assumed that the insulin sensitivity is increased when glucose plasma concentrations falls below basal value based on the risk function [12, 15]:

$$\dot{X}(t) = -p_2 \cdot X(t) + p_2 \cdot SI \cdot [I(t) - I_b] \quad X(0) = 0 \quad (6), (7)$$

$$\dot{G}(t) = \begin{cases} -[SG + X(t) \cdot (1 + r_1 \cdot \text{risk})] \cdot \\ G(t) + SG \cdot G_b + \frac{GIR(t)}{V} & \text{if } G(t) < G_n \\ -[SG + X(t)] \cdot G(t) + SG \cdot \\ Gb + \frac{GIR(t)}{V} G(0) = Gb & \text{otherwise} \end{cases} \quad G(0) = G_b$$

where G(t) is plasma glucose concentration, I(t) plasma insulin concentration, GIR(t) is exogenous glucose infusion rate, SG, SI, p2, V, r1 and r2 are model parameters.

Figure 3:
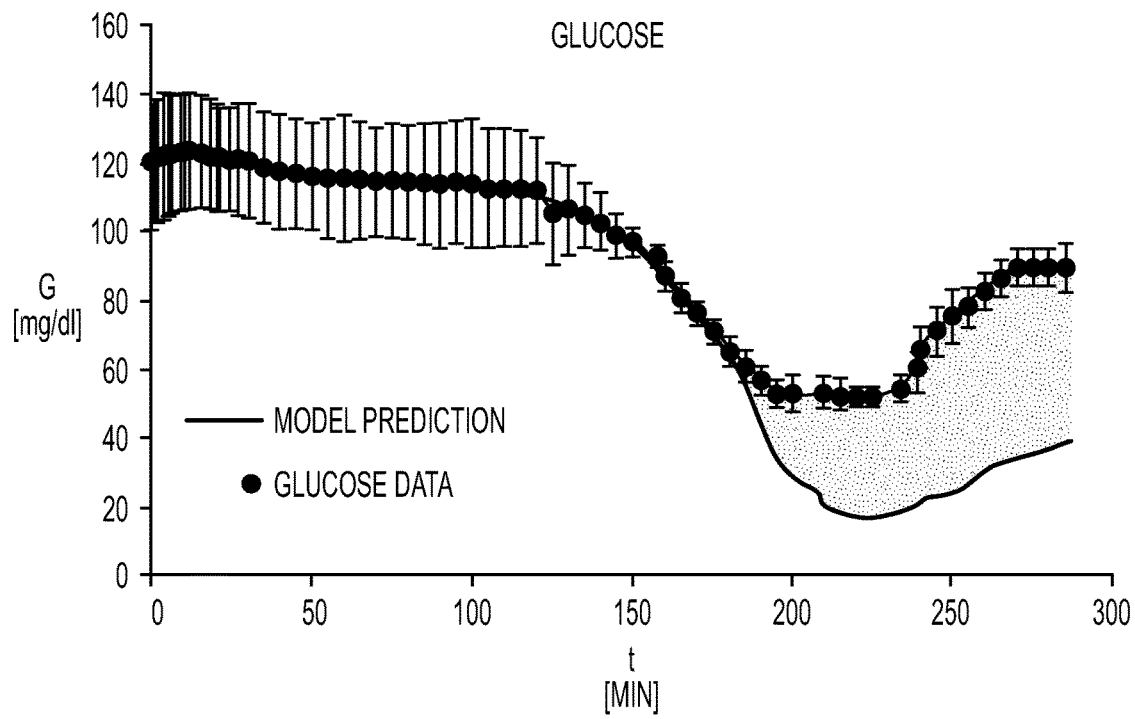
FIG. 3 is a graph showing average model prediction against glucose data in 32 T1DM subjects.

The model was fitted on blood glucose data. A glucose threshold of 60 mg/dl was defined together with its corresponding time t̂. The model was identified on blood glucose data for time 0≤t<t̂, while for t≥t̂, the model was used to predict the glucose data. Since this model cannot take into account the counter-regulation response to hypoglycemia, we expect that the prediction of the model G for t≥t̂ underestimates the glucose data. The model fits the data well including the rapid descent in hypoglycemia (FIG. 3) and provides precise estimates of the parameters [15].

2) Glucagon Secretion and Kinetics

A) the Model

The model of glucagon secretion and kinetics is described by the following equations:

$$\dot{G}n(t) = -k_{0Gn} \cdot Gn(t) + GSR(t) \quad Gn(0) = Gn_b \quad (8)$$

$$GSR(t) = Y_g(t) + k_{GSRd} \cdot \max\left(-\frac{dG(t)}{dt}, 0\right) \quad (9)$$

$$\dot{Y}_g(t) = -\alpha_g \cdot \left[Y_g - \max\left(\frac{k_{GSRs} \cdot [G_{Th} - G(t)]}{I(t) - I_{th} + 1} + GSR_b, 0\right)\right] \quad (10)$$

$$Y_g(0) = GSR_b$$

where Gn(t) is the plasma glucagon concentration, GSR(t) is the glucagon secretion, $GSR_b$ its basal value, $k_{0Gn}$ is glucagon clearance rate, G(t) is plasma glucose and I(t) is plasma insulin concentration, $G_{th}$ is the glucose threshold, $I_{th}$ a threshold above which plasma insulin inhibits glucagon secretion (usually close to the basal level), dG(t)/dt is the glucose rate of change, $k_{GSRs}$ the alpha-cell responsivity to glucose level, 1/αg the delay between static glucagon secretion and plasma glucose, and $k_{GSRd}$ the alpha-cell responsivity to glucose rate of change.

B) Model Assessment

Figure 4:
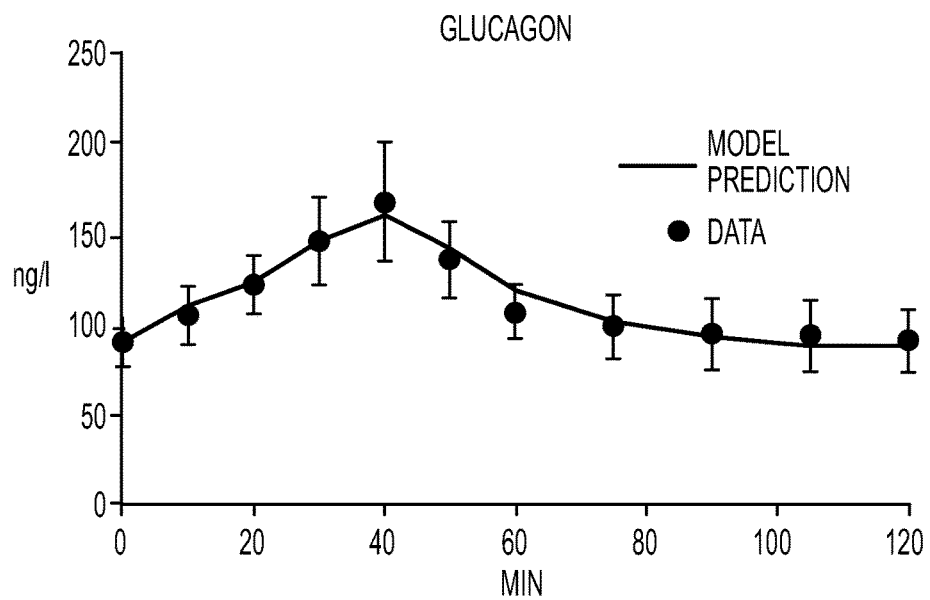
FIG. 4 is a graph showing average model prediction versus average plasma glucagon concentration in 13 healthy subjects.

The model has been assessed against data using the data base of 13 healthy patients undergoing insulin induced hypoglycemia [13]. Model prediction against data is shown in FIG. 4.

3) Glucagon Action

A) the Model

The model of glucagon action on endogenous glucose production is described by the following equations:

$$EGP(t) = k_{p1} - k_{p2} \cdot G_p(t) - k_{p3} \cdot X^L(t) + k_{counter} \cdot XGn(t)$$

$$\dot{I}'(t) = -k_i \cdot [I'(t) - I(t)] I'(0) = 0$$

$$\dot{X}^L(t) = -k_i \cdot [X^L(t) - I'(t)] X^L(0) = 0$$

$$\dot{X}Gn(t) = -k_{XGn} \cdot XGn(t) + k_{XGn} \cdot \max[(Gn(t) - Gn_b), 0] XGn(0) = 0 \quad (11)$$

where EGP(t) is endogenous glucose production, $G_p(t)$ is glucose amount in the plasma compartment, $X^L(t)$ is the delayed insulin action in the liver, XGn(t) the delayed glucagon action on EGP, Gn(t) is plasma glucagon concentration and $k_i$, $k_{p1}$, $k_{p2}$, $k_{p3}$, $k_{counter}$ and $k_{XGn}$ are model parameters.

B) Model Assessment

Figure 5:
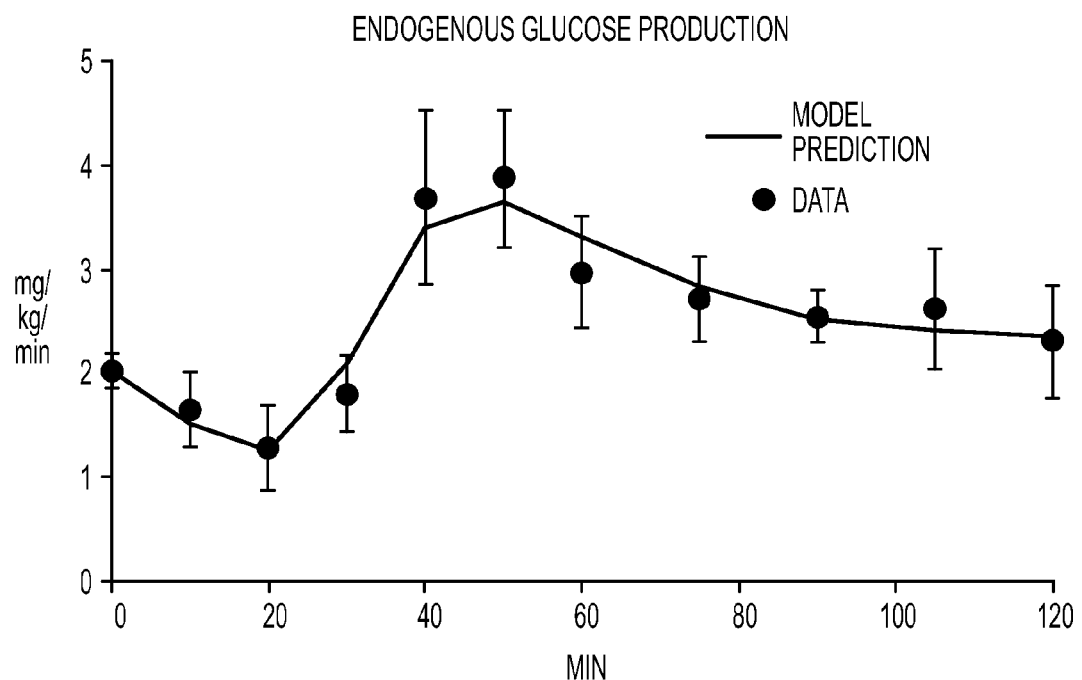
FIG. 5 is a graph showing average model prediction versus average endogenous glucose production in 13 healthy subjects.
Figure 6:
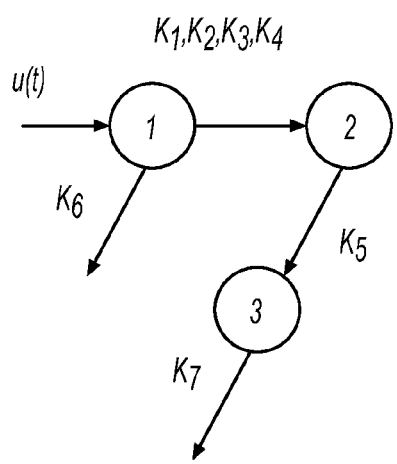
FIG. 6 is an SQ glucagon transport model diagram.
Figure 7:
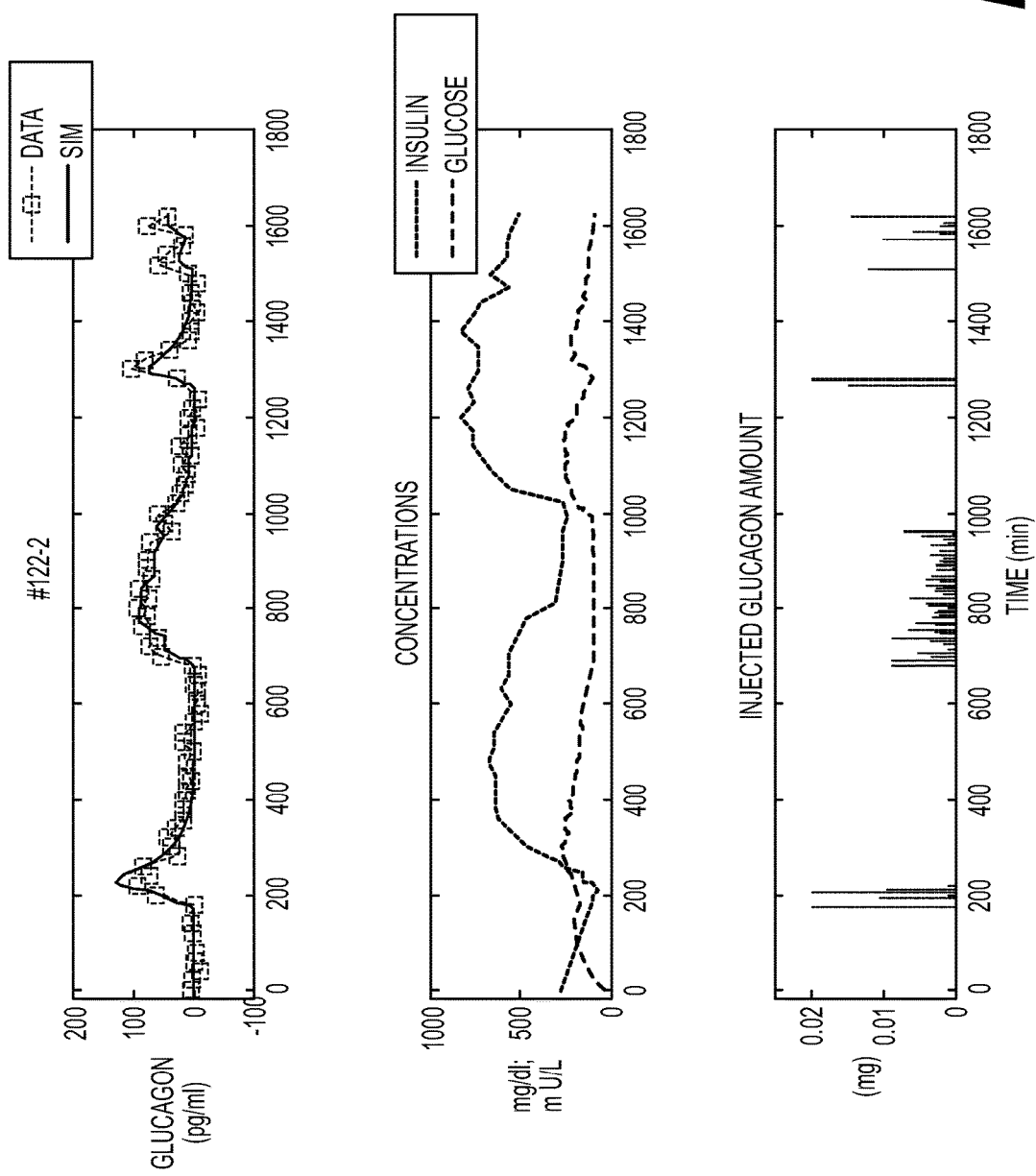
FIG. 7 is a comparative diagram showing an example of glucagon SQ transport model fit.

The model has been assessed against data using the same data set as above (13 healthy subjects [14]). Model prediction against data is shown in FIG. 5.

4) Modification Of The Joint Parameter Distribution

The inclusion of the risk function to the insulin dependent utilization makes the choice of the basal glucose (Gb) potentially critical. In fact insulin, sensitivity starts increasing following the risk function as soon as glucose falls below the basal value. In the previous release of the simulator, Gb was randomly generated from the joint distribution with an average of 140 mg/dl. However, Gb in the previous implementation was derived in health, pre-diabetes and T2DM corresponding to an existing concept of fasting glucose. Therefore, in T1DM, Gb should correspond to patient glucose target, since it is the glucose level reached with optimal basal insulin infusion, in absence of external perturbation, like meals and physical activity. Our recent clinical trial in type 1 diabetic patients [1-3] glucose target was around 120 mg/dl in average. Thus, joint parameter distribution was changed accordingly.

5) Glucagon Subcutaneous Transport

As the use of glucagon in a closed loop system has received more attention [e.g. 24], the use of a simulation platform becomes important for both control design and testing in the preclinical phase. Such functionality necessitates establishing a pharmacokinetic model of exogenous glucagon reproducing its appearance in plasma; its action being controlled by the model described previously.

A) Model:

$$\dot{x}_1(t) = -\left(k_1 + k_2 \frac{(x_1(t)/k_3)^{k_4}}{1 + (x_1(t)/k_3)^{k_4}}\right) x_1(t) - k_6 x_1(t)$$

$$\dot{x}_2(t) = -\left(k_1 + k_2 \frac{(x_1(t)/k_3)^{k_4}}{1 + (x_1(t)/k_3)^{k_4}}\right) x_1(t) - k_5 x_2(t)$$

$$\dot{x}_3(t) = k_5 x_2(t) - k_7 x_3(t)$$

where $x_3$ is the plasma glucagon concentration and both $x_1$ and $x_2$ are subcutaneous compartments. $k_5$ and $k_6$ correspond to degradation of glucagon in the subcutaneous tissues, $k_1$-$k_4$ describe a nonlinear transport in the subcutaneous tissues (with a slower time constant at lower doses), and $k_7$ corresponds to the plasma clearance.

B) Model Assessment

The clinical data used in this assessment comes from a bi-hormonal closed loop euglycemia control system developed by Dr. El-Khatib, et al. [24]. In their experimental design, there were a total of 11 adults with T1DM, who were failing to produce insulin. The demographic data were: age: 40±16 years, weight: 83±13 kg, BMI: 28±3 kg/m², diabetes duration: 23±13 years; HbA1c: 7.3±0.8%. These subjects were studied in a 27-hour span of time, during which they were given three regular carbohydrate-rich meals. Some subjects enrolled twice for the study, which were separated by at least 5 months. 13 data sets are available for analysis (some subjects were repeated). Plasma insulin and glucagon were measured frequently and injections of each hormone were recorded. Minimal deviation was observed in plasma glucagon between model predictions and collected data.

6) Generation of the Population

The new parameters $r_1$, $r_3$ were randomly generated from a joint distribution derived from [15] (r2 was derived from $r_1$ and $r_3$); while the SQ glucagon transport model parameters we generated using lognormal distributions had parameters as follows:

| parameters | μ | σ |
|---|---|---|
| $k_1$ | −5.3877 | 1.6259 |
| $k_2$ | −3.9327 | 1.3582 |
| $k_3$ | fixed at $5 \cdot 10^{-3}$ | |
| $k_4$ | fixed at 3.5 | |
| $k_5$ | −3.364 | 1.277 |
| $k_6$ | −1.1883 | 1.1558 |

Figure 8A:
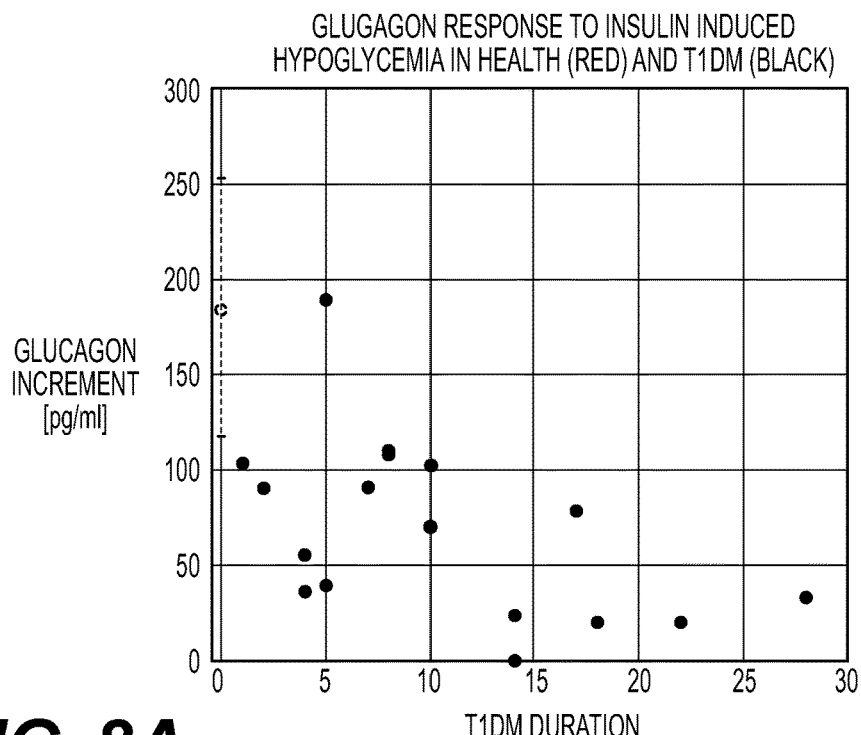
FIG. 8A-8B are charts showing glucagon counter-regulatory response wanes with duration of diabetes.

Generation of the glucagon secretion parameters was more complex as it has been shown that glucagon secretion is dependent on the duration of diabetes [25-27]. A reproduction of the data presented in [25] can be seen in FIG. 8A.

Figure 8B:
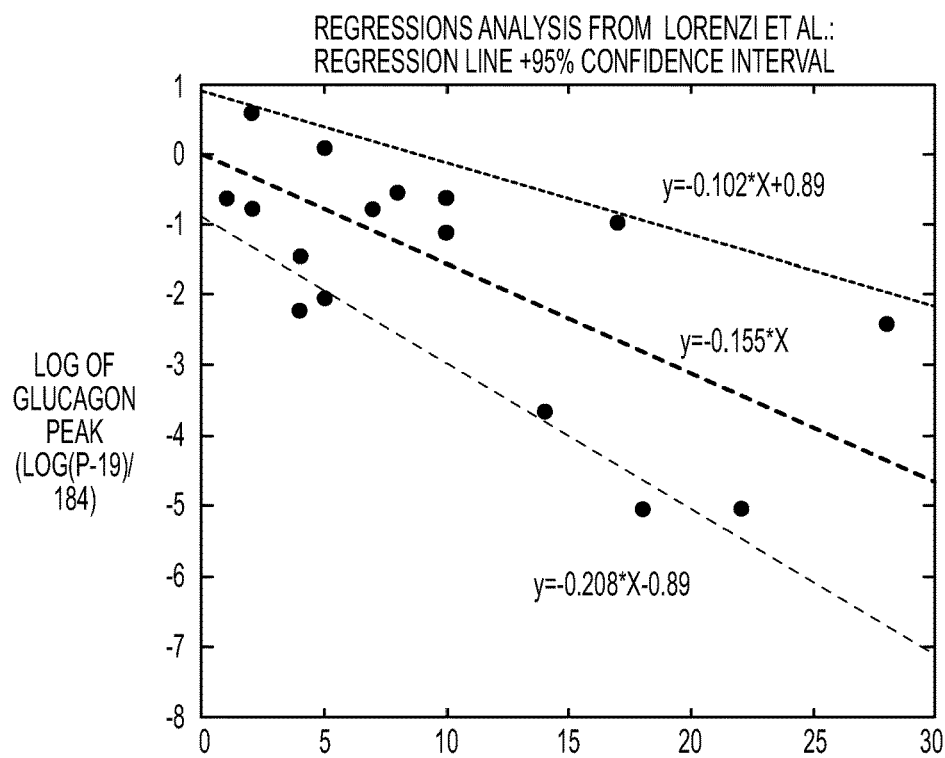
Figure 9:
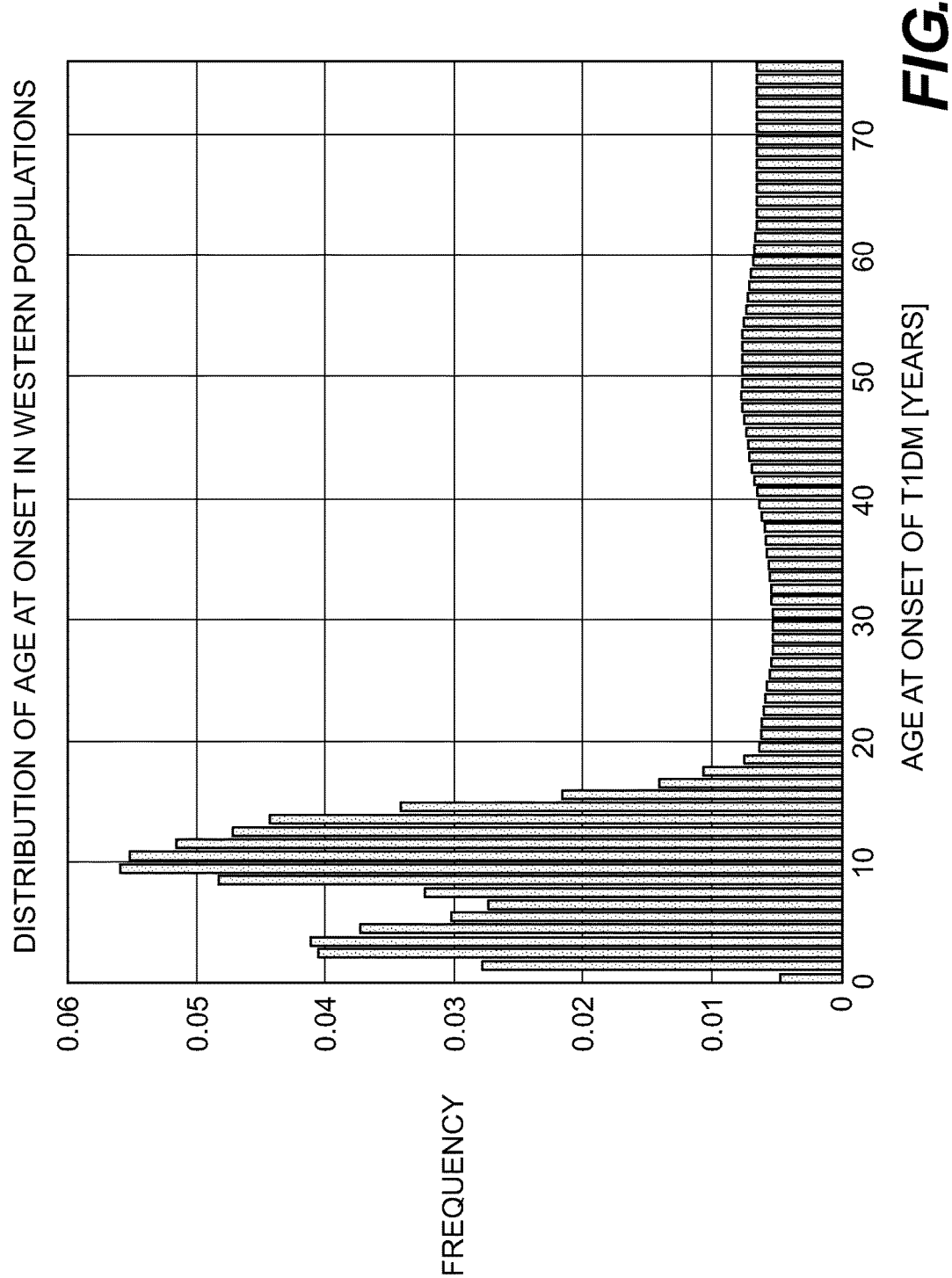
FIG. 9 is a graph showing age distribution with onset of T1DM.

Our prior work focused on the existence of a link between T1DM duration and counter-regulatory response, therefore using linear techniques (correlation). A more careful examination of the data shows a clear logarithmic relationship, which is presented in FIG. 8B. As the previously approved in-silico population does not contain duration of T1DM but only age, we need to associate duration of T1DM to each in-silico patient before we can appropriately generate their glucagon secretion parameters. Using literature on T1DM incidence [28-32] we generated a distribution of Age at Onset (which then can be easily transformed in T1DM duration by using the subject's age) as presented in FIG. 9. Random sampling from this distribution, conditioned by the age of the in-silico patient, allowed for the generation of the duration of T1DM for each in-silico patient while respecting the incidence characteristics of the disease. Mean of kGSRs and kGSRd (gains of the glucagon secretion model) were adjusted to reflect the dependency observed in FIG. 9, while other parameters as well as the covariance matrix were kept constant. Once T1DM duration was generated for each in-silico subject, a T1DM duration dependent set of glucagon secretion parameter was generated.

Figure 10A:
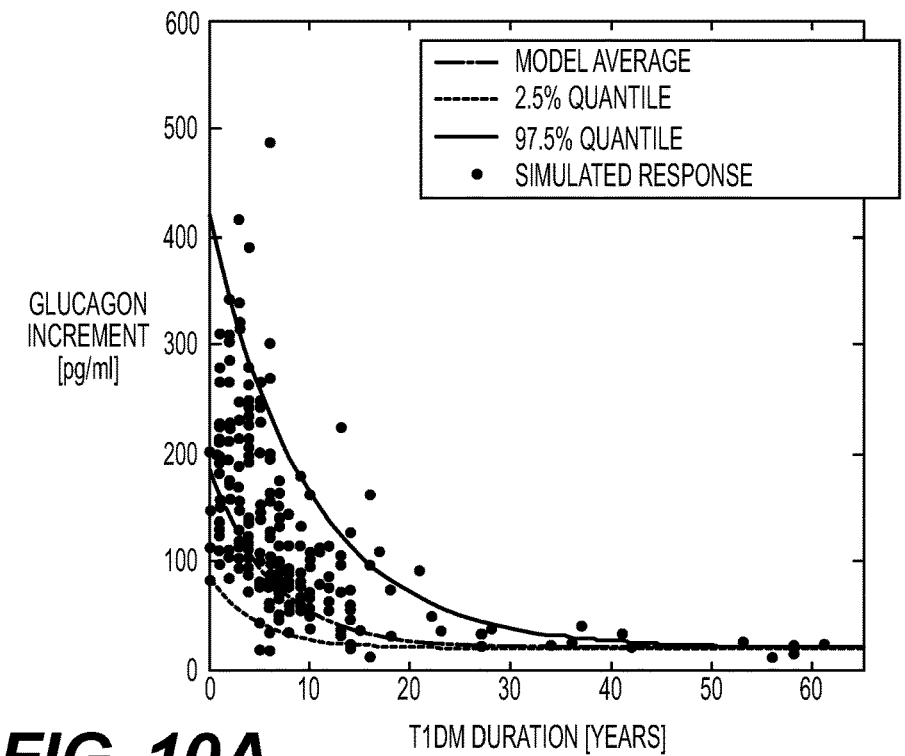
FIGS. 10A-10B are charts showing in-silico glucagon response to insulin induced hypoglycemia.
Figure 10B:
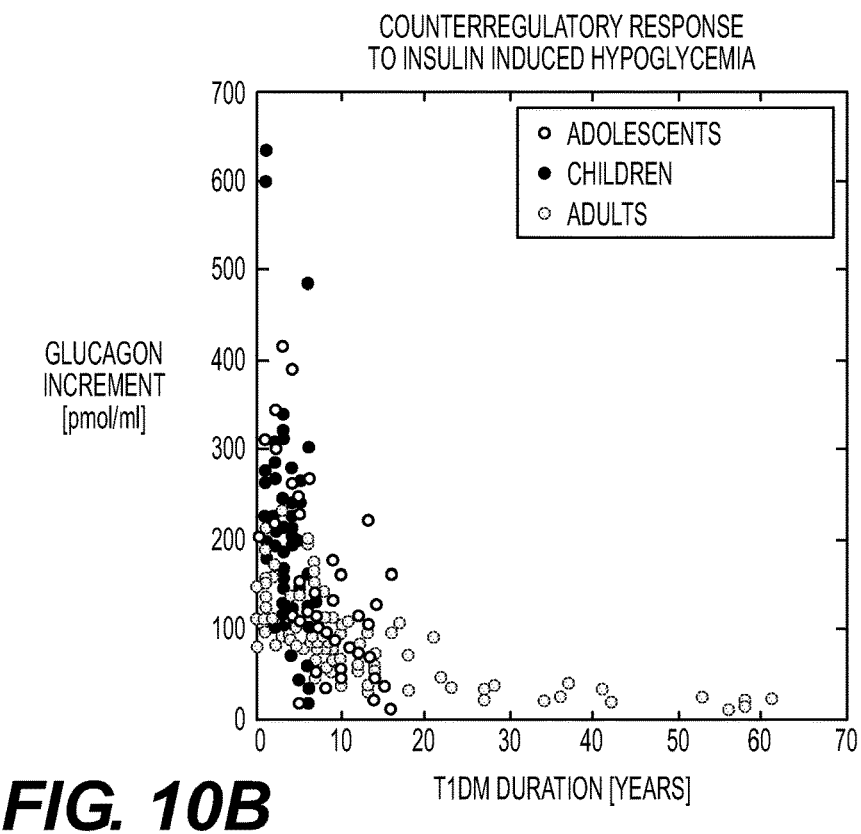

To verify that parameters were properly generated we simulated the experiment described in [25] and computed the glucagon increment for each in-silico subject. Results are presented in FIG. 10.

Determination of CR and CF

In real patients CR (carbohydrate ratio) and CF (correction factor) are empirically determined from patient history, habits and physician experience. At variance with the first release of the T1DM simulator, where some computationally optimal definition of CR and CF were used, here we used the following definitions, which mimic as much as possible the criterion used to empirically determine them in real patients [17-20].

CR was determined with the following simulation: each subject receives 50 g of CHO, starting from basal level. The optimal insulin bolus is determined so that the postprandial glucose (Gpostprand), i.e. glucose concentration measured 3 hours after the meal, is between 85% and 110% of the basal the minimum glucose concentration is above 90 mg/dl the maximum glucose concentration is between 40 and 80 mg/dl above the basal level. Then, CR is calculated as the ratio between the amount of ingested CHO and the optimal insulin bolus:

$$CR = \frac{\text{ingested } CHO}{\text{optimal bolus}} \quad (12)$$

CF was determined with the so called 1700 rule [20], i.e.

$$CF = \frac{1700}{TDI} \quad (13)$$

where TDI is the total daily insulin, determined for each virtual patient, using optimal CR and basal infusion rate, and assuming an average diet of 180 g of CHO.

New Criteria for Virtual Subject Generation

In the previous release of the simulator, the virtual subjects were randomly extracted from an appropriate joint parameter distribution. However, due to randomness of the generation process, the procedure can potentially lead to implausible behavior for some in-silico patients. Thus, in this release of the T1DM simulator, we introduced new criteria for virtual subject generation. In particular, subjects who met the following criteria have been included in the new in-silico adult population:

CR≤30 g/U

Mahalanobis distance lower than that corresponding to the 95% percentile kmax>kmin kmin>0.008 b<1

Updated Virtual Patient Population

Figure 11:
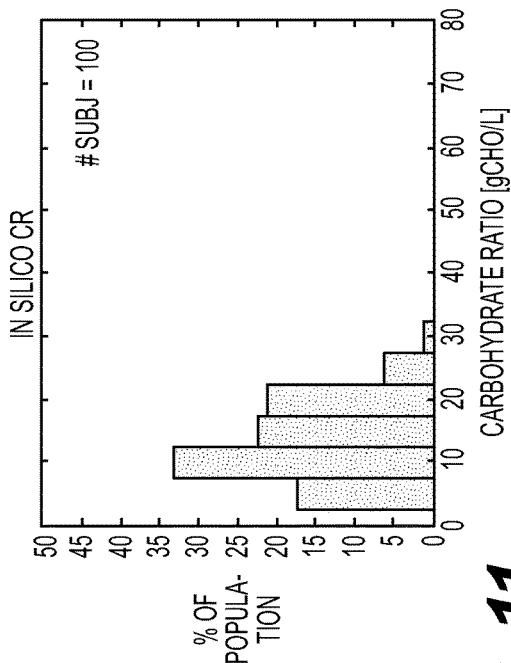
FIG. 11 is a pair of graphs showing real versus in-silico CR distributions.
Figure 12:
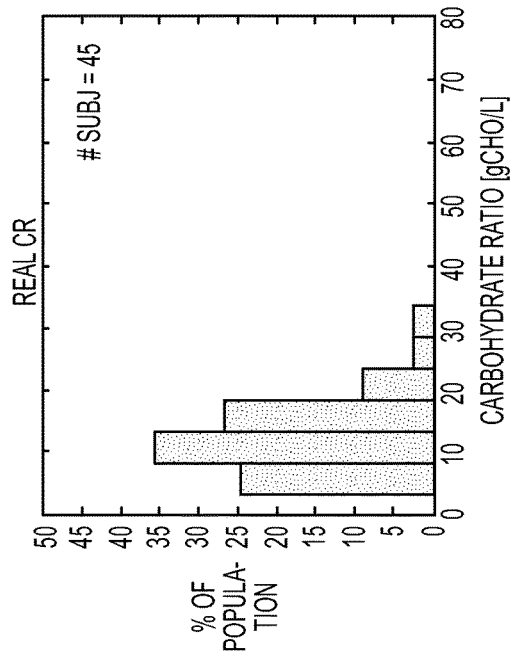
FIG. 12 is a graph showing distribution of adult in-silico CF.
Figure 12:
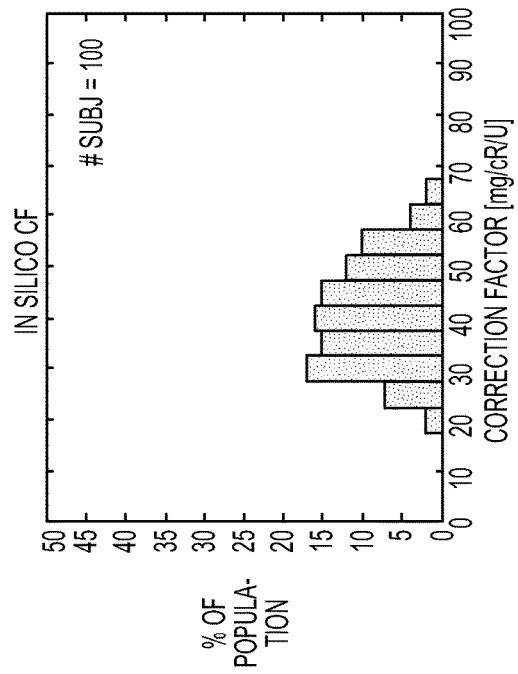

One hundred in-silico adults were generated using the above described criteria. Model parameters of the 300 in-silico subjects are reported in Appendix A2. The distributions of real and in-silico CR are shown in FIG. 11, while the distributions in-silico CF are shown in FIG. 12.

Assessment Of The Clinical Validity Of The T1DM Simulator

Test 1

Database

The database used to assess the clinical validity of the T1DM simulator consisted of 24 T1DM adult subjects [1-3], recruited at the Universities of Virginia (N=11), Padua, Italy (N=7) and Montpelier, France (N=6). Each patient had two 22 h hospital admissions (from 3 pm to 1 pm on the following day), one in open- and one in closed-loop, respectively. Briefly, during both inpatient admissions subjects received dinner (70.7±3.3 g of CHO) between 6 and 7 pm and breakfast (52.9±0.1 g of CHO) between 7 and 8 am, and their plasma glucose was frequently measured (see [3] for details). Each glucose trace was subdivided into post-dinner (from dinner ingestion to 5 hours later), overnight (from 5 hours after dinner to the beginning of breakfast) and post-breakfast (from breakfast ingestion to 5 hours later); for model assessment, post-dinner and post-breakfast traces have been used, for a total of 96 post-meal traces.

Assessment of Simulator Clinical Validity

In order to prove that the simulator is valid from the clinical point of view it is required that for each real type 1 diabetic subject, a virtual subject exists, which, if having undergone the same experimental scenario, behaves similarly to the real subject from a behaviour clinical point of view, i.e., it does not necessarily perfectly fit the real glucose profile, but shows a similar pattern and lies in the same clinically relevant zone (hypoglycemia, euglycemia, hyperglycemia). The distribution of the most important outcome measures in the simulated traces reproduces the one observed in real experiments.

Thus, to test the first requirement, for each trace of the database, measured plasma glucose profiles were compared with those simulated in 100 in-silico adults, obtained with the same experimental scenario. Among the 100 simulated profiles, the one that best fitted the real data was selected and compared with the real glucose profile using the Continuous Glucose Error Grid Analysis (CG-EGA) [21]. This method was originally developed for the clinical evaluation of Continuous Glucose Monitoring (CGM) systems in terms of both accurate blood glucose (BG) readings and accurate direction and rate of BG fluctuations. It provides a Point-Error Grid Analysis (P-EGA), combined with a Rate-Error Grid Analysis (R-EGA) and an error matrix (EM). P-EGA and R-EGA plot CGM versus BG and CGM rate of change versus BG rate of change, respectively on a plane divided into specific zones, which take into account the dangerousness of erroneous readings in relation to the actual glucose level [8]. The error matrix summarizes the results of the analysis, reporting the percentages of accurate readings, benign errors and erroneous readings of P-EGA and R-EGA. Here we use the above described tool to compare simulated with real glucose profiles.

For what concerns the second requirement, the distribution of mean glucose (MEAN(G)), intra-subject interquartile range (IQR(G)) low and high blood glucose indices (LBGI, HBGI) [19], obtained in real and simulated experiments, have also been compared.

Results

Figure 13:
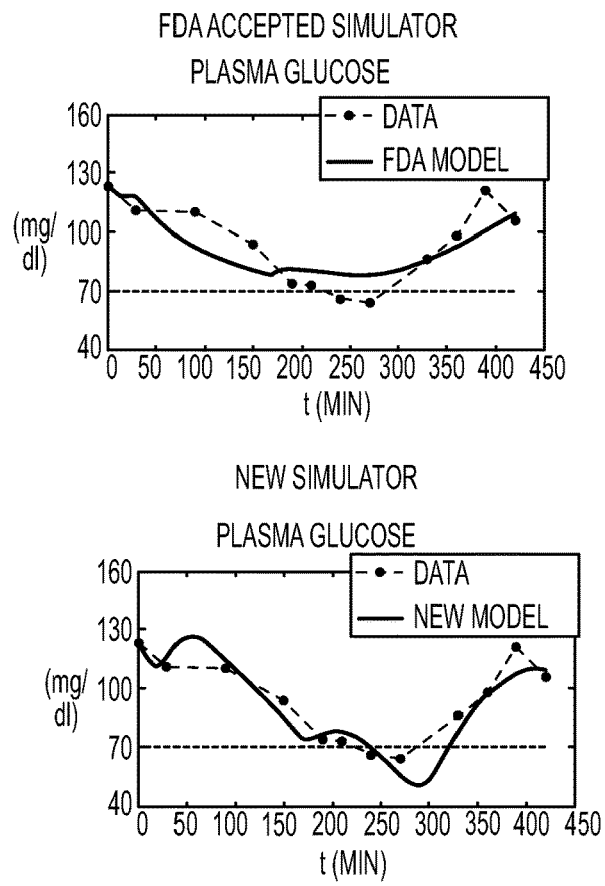
FIG. 13 is a pair of plots showing a comparison of read data versus simulations in two illustrative subjects, for the FDA accepted simulator (left) and the new simulator in accordance with the invention (right)

FIG. 13 shows the comparison between measured plasma glucose data and the simulated profiles of the FDA accepted model both without (left panels) and with the above hypoglycemia modification (right panels) in two illustrative cases. It is worth noting that the simulated profiles obtained with the original FDA simulator reproduce quite well the real glucose patterns in euglycemia and hyperglycemia, but the glucose decreases are not rapid enough, so that the hypoglycemic episodes are not well predicted. On the other hand, with the introduction of the new description of glucose utilization in hypoglycemia and counter-regulation of the present invention, the glucose falls occur more rapidly and the hypoglycemic episodes predicted by the simulator reflect that observed during clinical trials.

CG-EGA was applied first on measured data and simulations obtained with the original FDA accepted simulator. The average results (Table 1, 1$^{st}$ row) are very good in euglycemia and hyperglycemia (% in Accurate+Benign zones: 99.9% in euglycemia; 99.5% in hyperglycemia), less in hypoglycemia (% in Accurate+Benign zones: 35.6%). Results of CG-EGA applied to measured data and simulations obtained with the new model (Table 1, 2$^{nd}$ row) are similar to the previous one in euglycemia and hyperglycemia (% in Accurate+Benign zones: 99.9% in euglycemia; 99% in hyperglycemia), while they are significantly improved in hypoglycemia (% in Accurate+Benign zones: 87.3%). It is of note that the results obtained at single individual level are not substantially different from the average ones.

The results presented above, are confirmed by the results reported in Table 2. The comparison between real data and simulations, obtained with the original FDA approved simulator shows that MEAN(G) is similar in simulations, IQR (G), LBGI and HBGI are lower (p-value <0.05) in simulated vr real experiments. On the other hand, the comparison between real data and simulations obtained with the new model provides significantly better results: all the outcome measures are not significantly different in real and simulated trials (p-value >0.05). We conclude that with the modifications described in this document, the FDA accepted simulator, is valid from the clinical point of view.

TABLE 1

CG-EGA: FDA Simulator vs. New Simulator

| | Hypoglycemia | | | Euglycemia | | | Hyperglycemia | | |
|---|---|---|---|---|---|---|---|---|---|
| | Accurate | Benign | Bad | Accurate | Benign | Bad | Accurate | Benign | Bad |
| FDA Model | 35.6% | 0.0% | 64.4% | 99.1% | 0.8% | 0.1% | 98.8% | 0.7% | 0.5% |
| New Model | 86.6% | 0.7% | 12.7% | 99.3% | 0.6% | 0.1% | 98.1% | 0.9% | 1.0% |

Table 1 shows CG-EGA of real and simulated experiments obtained with the FDA accepted and the new simulators.

TABLE 2

| Outcome Measures | | | |
|---|---|---|---|
| | Real Data | Simulations (FDA Model) | Simulations (New Model) |
| Mean(G) | 156.9 ± 41.3 | 158.0 ± 42.5 (0.304) | 157.0 ± 44.62 (0.944) |
| IQR(G) | 71.2 [50.9-96.1] | 57.9 [32.5-80.3] (<0.0001) | 64.7 [46.0-86.5] (0.196) |
| LBGI | 0.59 [0.02-2.22] | 0.19 [0.00-1.42] (<0.0001) | 0.38 [0.00-2.27] (0.328) |
| HBGI | 4.85 [1.79-8.34] | 4.11 [1.77-8.21] (0.030) | 4.11 [1.46-8.34] (0.846) |

Table 2 shows a comparison between outcome measures of real and simulated experiments. Values are mean±SD for normally distributed variables (p-value from paired T-test) or median [interquartile range] for not normally distributed variables (p-value from Wilcoxon Signed Rank Test).

Test 2

Database

The database used to assess the clinical validity of the T1DM simulator consisted of 9 T1DM adult subjects [33], recruited at the University of Virginia. Each patient had two 22 h hospital admissions (from 11 am to 9 am on the following day), one in open- and one in closed-loop, respectively. Briefly, during both inpatient admissions subjects received lunch at 11 am, dinner between 6 and 7 pm and breakfast between 7 and 8 am and exercised at 4 pm. Plasma glucose was frequently measured (see [33] for details). Only lunch was used for this analysis (11 am-4 pm) as exercise effects are not yet implemented in the simulation platform.

Assessment of Simulator Clinical Validity

In order to prove that the simulator is valid from the clinical point of view it is required that for each real type 1 diabetic subject, a virtual subject exists, which, if having undergone the same experimental scenario, behaves similarly to the real subject from a behavioural clinical point of view, i.e., it does not necessarily perfectly fit the real glucose profile, but shows a similar pattern and lies in the same clinically relevant zone (hypoglycaemia, euglycemia, hyperglycemia).

Thus, to test the first requirement, for each trace of the database, measured plasma glucose profiles have been compared with those simulated in 100 in-silico adults, obtained with the same experimental scenario. Among the 100 simulated profiles, the one that best fitted the real data was selected and compared with the real glucose profile using the Continuous Glucose Error Grid Analysis (CG-EGA) [21].

Results

As shown in Table 3 Table 3, out of 18 admissions only two resulted in <90% overall agreement between simulation and in-vivo data. Both instances were due to missed hypoglycemic events, while otherwise agreement was 93% in hypoglycemia, 99.6% in euglycemia and 100% in hyperglycemia, demonstrating very robust performance of the new simulation platform.

TABLE 3

Simulation fit to in-vivo data collected during AP inpatient study

| Patient ID | Sim ID | MARD % | CEGA (A + B) % | CGEGA (A + B, <70 mg/dl) % | CGEGA (A + B, [70 180] mg/dl) % | CGEGA (A + B, >180 mg/dl) % | CGEGA (A + B) % |
|---|---|---|---|---|---|---|---|
| 101-1 | 71 | 8.25 | 100 | — | 100 | 100 | 100 |
| 101-2 | 40 | 25.25 | 100 | — | 100 | — | 100 |
| 102-1 | 71 | 15.41 | 100 | 100 | 100 | 100 | 100 |
| 102-2 | 63 | 16.67 | 100 | — | 100 | 100 | 100 |
| 104-1 | 98 | 20.64 | 100 | — | 100 | 100 | 100 |
| 104-2 | 46 | 15.70 | 100 | 100 | 100 | — | 100 |
| 105-1 | 32 | 18.32 | 100 | — | 92.86 | 100 | 93.75 |
| 105-2 | 37 | 24.94 | 94.74 | 80 | 100 | — | 94.44 |
| 107-1 | 13 | 31.08 | 88.89 | 0 | 100 | 100 | 88.24 |
| 107-2 | 100 | 11.23 | 100 | — | 100 | 100 | 100 |
| 109-1 | 24 | 6.19 | 100 | — | 100 | 100 | 100 |
| 109-2 | 26 | 7.21 | 100 | — | 100 | 100 | 100 |
| 110-1 | 66 | 19.04 | 100 | 80 | 100 | 100 | 94.12 |
| 110-2 | 57 | 10.96 | 100 | 100 | 100 | — | 100 |
| 111-1 | 66 | 13.58 | 100 | 100 | 100 | — | 100 |
| 111-2 | 9 | 24.85 | 87.5 | 0 | 100 | — | 86.67 |
| 112-1 | 100 | 12.07 | 100 | — | 100 | 100 | 100 |
| 112-2 | 79 | 8.40 | 100 | — | 100 | 100 | 100 |

Figure 14:
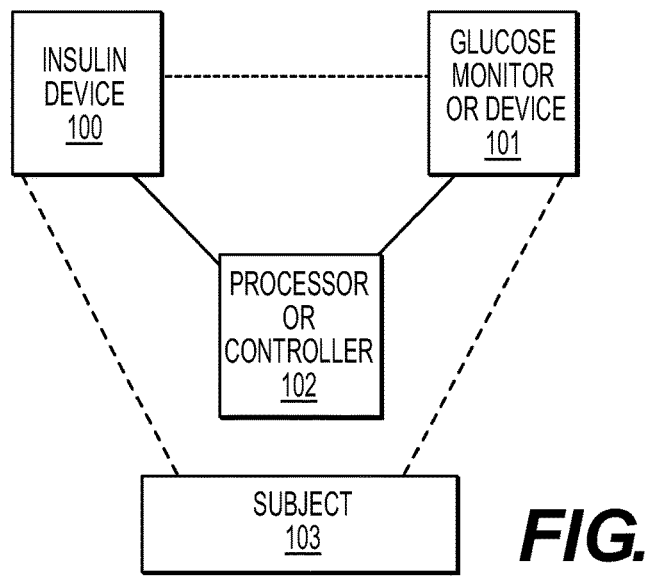
FIG. 14 is a high level functional block diagram of an example embodiment of the present invention.

FIG. 14 is a high level functional block diagram of an embodiment of the present invention, or an aspect of an embodiment of the present invention.

As shown in FIG. 14, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 15A:
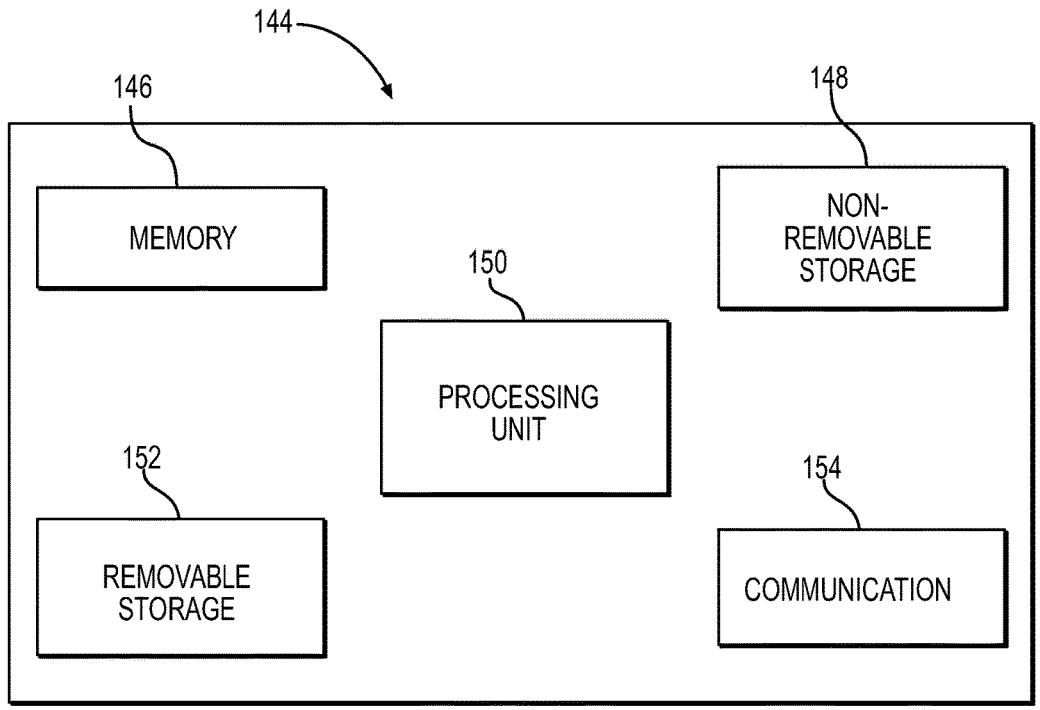
FIG. 15A is a functional block diagram of an example computer system in which the present invention may be implemented.

Referring to FIG. 15A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media. In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections.

Figure 15B:
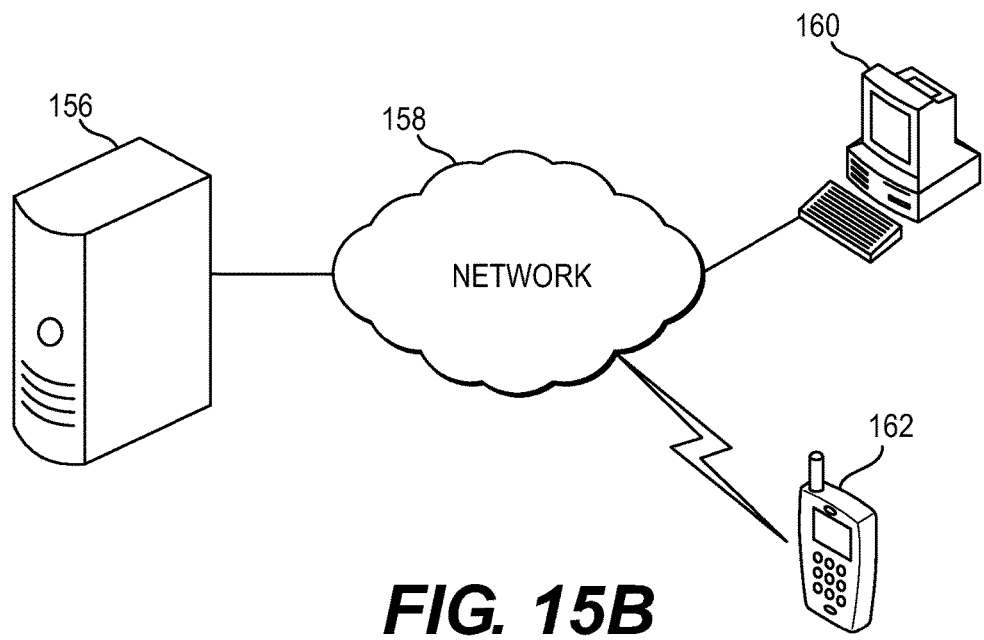
FIG. 15B is a diagram of a network system in which embodiments of the invention may be implemented.

As a way of example, FIG. 15B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and/or an insulin device. Any of the components shown or discussed with FIG. 15B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device; and/or insulin device or pump), whereas other processing and execution of the instruction can be performed at another computing device (e.g. terminal 160) of the network system, or vice versa. In fact, certain processing or execution can be performed at one computing device (e.g. server 156 and/or glucose monitor device; and/or insulin device or pump); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 16:
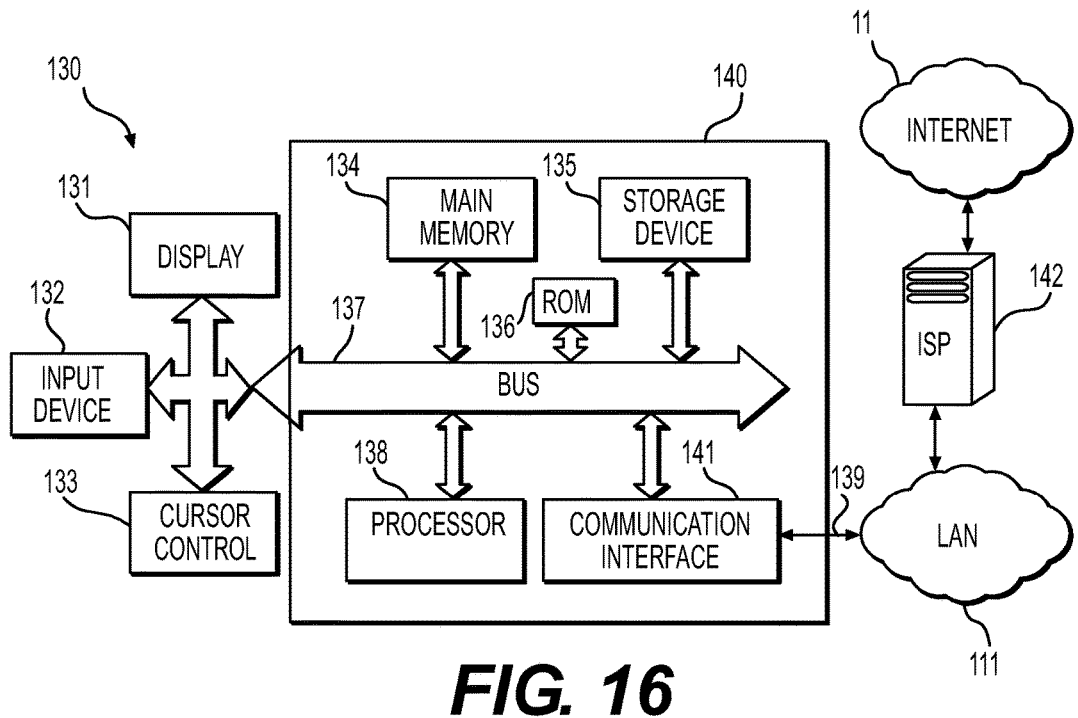
FIG. 16 is a block diagram of another example computer system in which the present invention may be implemented.

FIG. 16 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 16. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 16 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 16 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100 BaseT, 1000 BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave. The concept of, among other things, reliable framework for in-silico trials, for testing and improving glucose sensors and insulin augmented pumps (devices) prediction and operation methods, and for closed loop single/dual hormone controller design, testing, and validation has been developed. As seen from the algorithm and methodology requirements discussed herein, the techniques and approaches may be implemented and utilized with the related processors, networks, computer systems, internet, and components and functions according to the schemes disclosed herein.

Figure 17:
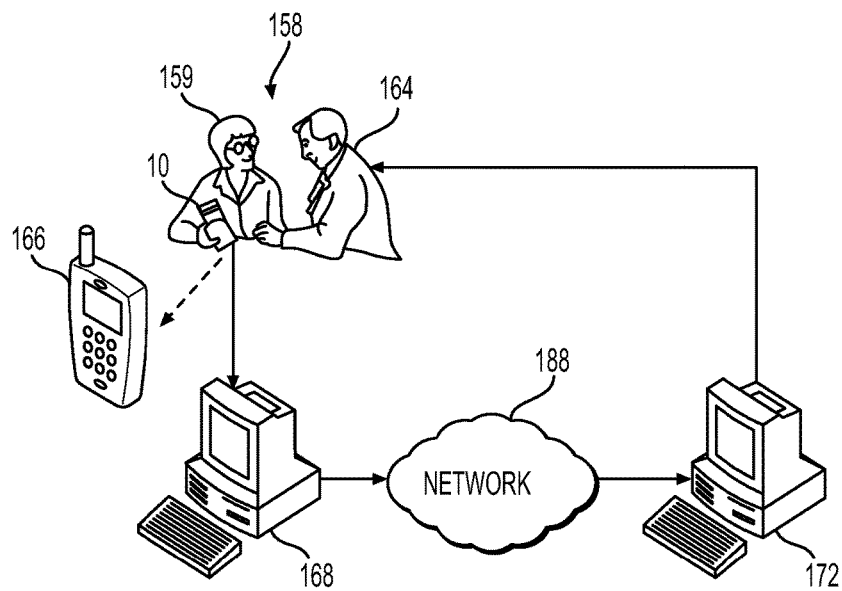
FIG. 17 is a diagram of another example of a network system in which embodiments of the invention may be implemented.

FIG. 17 illustrates a system in which one or more embodiments of the invention can be implemented using a network, or portions of a network or computers. Although the present invention glucose device may be practiced without a network.

FIG. 17 diagrammatically illustrates an exemplary system in which examples of the invention can be implemented. In an embodiment the glucose monitor (and/or insulin device or pump) may be implemented by the subject (or patient) locally at home or other desired location. However, in an alternative embodiment it may be implemented in a clinic setting or assistance setting. For instance, referring to FIG. 17, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 (and/or insulin device or pump) is shown in the figure, the system of the invention and any component thereof may be used in the manner depicted by FIG. 17. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 15A.

REFERENCES

The following patents, applications and publications as listed below and throughout this document are hereby incorporated by reference in their entirety herein.

1. Bruttomesso D, Farret A, Costa S, Marescotti M C, Vettore M, Avogaro A, Tiengo A, Dalla Man C, Place J, Facchinetti A, Guerra S, Magni L, De Nicolao G, Cobelli C, Renard E, Maran A. Closed-loop artificial pancreas using subcutaneous glucose sensing and insulin delivery and a model predictive control algorithm: preliminary studies in Padova and Montpellier. J Diabetes Sci Technol. 2009 Sep. 1; 3(5):1014-21.
2. Clarke W L, Anderson S, Breton M, Patek S, Kashmer L, Kovatchev B. Closed-loop artificial pancreas using subcutaneous glucose sensing and insulin delivery and a model predictive control algorithm: the Virginia experience. J Diabetes Sci Technol. 2009 Sep. 1; 3(5):1031-8.
3. Kovatchev B, Cobelli C, Renard E, Anderson S, Breton M, Stephen P, Clarke W, Bruttomesso D, Maran A, Costa S, Avogaro A, Dalla Man C, Facchinetti A, Magni L, De Nicolao G, Place J, Farret A. Multinational Study of Subcutaneous Model-Predictive Closed-LoopControl in Type 1 Diabetes Mellitus: Summary of the Results. J Diabetes Sci Technol. 2010; 4(6):1374-1381.
4. Breton M D, Bruttomesso D, Farret A, et al. Fully-integrated artificial pancreas in type 1 diabetes: modular closed-loop glucose control maintains near-normoglycemia. Diabetes. In Press. DOI 10.2337/db11-1445.
5. Dalla Man C, Raimondo D M, Rizza R A, Cobelli C. G I M, Simulation Software of Meal Glucose-Insulin Model. J Diabetes Sci Technol. 2007; 1(3):323-330.
6. Dalla Man C, Rizza R A, Cobelli C. Meal simulation model of the glucose-insulin system. IEEE Trans Biomed Eng. 2007; 54(10):1740-1749.
7. Dalla Man C, Camilleri M, Cobelli C. A System Model of Oral Glucose Absorption: Validation on Gold Standard Data. IEEE Trans Biomed Eng. 2006; 53(12):2472-2478.
8. Kovatchev B P, Breton M, Dalla Man C, Cobelli C. In-silico preclinical trials: a proof of concept in closed-loop control of type 1 diabetes. J Diabetes Sci Technol. 2009; 3(1):44-55.
9. Basu R, Dalla Man C, Campioni M, Basu A, Klee G, Jenkins G, Toffolo G, Cobelli C, Rizza R A. Effect of age and sex on postprandial glucose metabolism: difference in glucose turnover, insulin secretion, insulin action, and hepatic insulin extraction. Diabetes 2006; 55:2001-2014.
10. MAF 15021
11. Visentin R., Dalla Man C., Kovatchev B. P., Cobelli C. "Incorporating Nonlinear Response to Hypoglycemia into the Type 1 Diabetes Simulator". Book of Abstracts, pp. A183. 11th Diabetes Technology Meeting (DTM11), 27-29 Oct. 2011, San Francisco (Calif., USA).
12. Kovatchev B P, Straumea M, Cox D J, Farhya L S. Risk analysis of blood glucose data: A quantitative approach to optimizing the control of insulin dependent diabetes. J Theor Med. 1999; 3:1-10.
13. Micheletto F, Dalla Man C, Vella A, Cobelli C. A Model of Glucagon Secretion and Action in Healthy Subjects. Book of Abstracts. 10$^{th}$ Diabetes Technology Meeting (DTM). 2010, Bethesda, Md., USA, November 11-13; pp. A105.
14. Robert A. Rizza, Philip E. Cryer, and John E. Gerich. Role of Glucagon, Catecholamines, and Growth Hormone in Human Glucose Counterregulation. J. Clin. Invest. Volume 64 July 1979 62-7.
15. Micheletto F, Dalla Man C, Breton M D, Kovatchev B P, Cobelli C. A Counter-Regulation Model in Type 1 Diabetes. Book of Abstracts. 11$^{th}$ Diabetes Technology Meeting (DTM). 2011, Burlingame, Calif., USA, October 27-29; pp. A106.

16. Bergman R N, Ider Y Z, Bowden C R, Cobelli C. Quantitative estimation of insulin sensitivity. Am J Physiol. 1979 June; 236(6):E667-77.Bergman Ider Cobelli 1979
17. Warshaw H, Bolderman K M: Practical Carbohydrate Counting: A how-to-teach Guide for health professionals. Alexandria, Va., American Diabetes Association, 2001.
18. Walsh J, Roberts R. Setting and testing your Carb Boluses. In "Pumping Insulin. Everithing you need for success with an insulin pump". 3rd ed. Torrey Pines Press, San Diego, Calif., pag. 105-113, 2000.
19. Bolderman K M. Prepping pump patients. In "Putting your patients on the pump". ADA eds., Alexandria, Va., pag. 19-38, 2002.
20. Davidson P C, Hebblewhite H R, Bode B W, Steed R D, Welch N S, Richardson P L, Johnson J. Statistically-based CSII parameters: correction factor, CF (1700 rule), carbohydrate-insulin ratio, CIR (2,8 rule), and basal-to-total ratio (abstract). Diabetes Technol Ther 5 (2): 237, 2003.
21. Kovatchev B P, Cox D J, Gonder-Frederick L A, Clarke W L. Methods for quantifying self-monitoring blood glucose profiles exemplified by an examination of blood glucose patterns in patients with type 1 and type 2 diabetes. Diabetes Technol Ther. 2002; 4:295-303.
22. Kovatchev B P, Cox D J, Gonder-Frederick L A, Young-Hyman D, Schlundt D, Clarke W L. Assessment of risk for severe hypoglycemia among adults with IDDM: validation of the low blood glucose index. Diabetes Care. 1998; 21:1870-1875.
23. Chan, L. Heinemann, S. Anderson, M. D. Breton, B. P. Kovatchev, Nonlinear Metabolic Effect of Insulin across the Blood Glucose Range in Patients with Type 1 Diabetes Mellitus, Journal of Diabetes Science and Technology, January 2010, 4(4): 873-881
24. F. H. El-Khatib, S. J. Russell, D. M. Nathan, R. G. Sutherlin, and E. R. Damiano, "A bihormonal closed-loop artificial pancreas for type 1 diabetes", *Science Translational Medicine*, vol. 2, no. 27, Apr. 2010.
25. Lorenzi M, Bohannon N, Tsalikian E, et al: Duration of type I diabetes affects glucagon and glucose responses to insulin-induced hypoglycemia [Clinical Investigation]. West J Med 1984 October; 141:467-471
26. Siafarikas A. et al. Early loff of Glucagon response to hypoglycemia in adolescents with type 1 diabetes. Diabetes Care published ahead of print June 2012.
27. Sjöberg A. et al., Residual insulin secretion is not coupled to a maintained glucagon response to hypoglycaemia in long-term type 1 diabetes. J. Intern. Med. 2002; 252: 342-351
28. Bruno G et al., Incidence of Type 1 and Type 2 Diabetes in Adults Aged 30-49 Years. *Diabetes Care* 28:2613-2619, 2005
29. Felner E. I. et al. Genetic interaction among three genomic regions creates distinct contributions to early- and late-onset type 1 diabetes mellitus. Pediatric Diabetes 2005, 6: 213-220
30. Laakso M., Pyörälä K., Age of Onset and Type of Diabetes, Diabetes Care 1985, 8 (2) 114-117
31. Karjalainen J et al. A comparison of childhood and adult type 1 diabetes mellitus. NEJM 1989 320(14): 881-886
32. Tenconi M. T. et al., IDDM in the province of Paviat, Italy, from a population-based registry. Diabetes Care 1995, 18(7): 1017-1019
33. Breton M. D., Farret A., Bruttomesso D., et al. Fully Integrated Artificial Pancreas in Type 1 Diabetes: Modular Closed-Loop Glucose Control Maintains Near Normoglycemia Diabetes September 2012 61:2230-2237

The devices, systems, computer readable medium, algorithms, models, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

a. U.S. patent application Ser. No. 13/637,359 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES," filed Sep. 25, 2012; U.S. Patent Application Publication No. 2013-0079613, Mar. 28, 2013. (01733-04)

b. International Patent Application No. PCT/US2011/029793 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES," filed Mar. 24, 2011; U.S. Patent Application Publication No. WO 2011/119832, Sep. 29, 2011. (01733-02)

c. U.S. patent application Ser. No. 13/634,040 entitled "Method and System for the Safety, Analysis, and Supervision of Insulin Pump Action and Other Modes of Insulin Delivery in Diabetes," filed Sep. 11, 2012. (01727-06)

d. International Patent Application No. PCT/US2011/028163 entitled "Method and System for the Safety, Analysis, and Supervision of Insulin Pump Action and Other Modes of Insulin Delivery in Diabetes," filed Mar. 11, 2011. (01727-02)

e. U.S. patent application Ser. No. 13/393,647 entitled "System, Method and Computer Program Product for Adjustment of Insulin Delivery (AID) in Diabetes Using Nominal Open-Loop Profiles," filed Jun. 15, 2012. (01689-06)

f. International Patent Application No. PCT/US2010/047386 entitled "System, Method and Computer Program Product for Adjustment of Insulin Delivery (AID) in Diabetes Using Nominal Open-Loop Profiles," filed Aug. 31, 2010. (01689-02)

g. U.S. patent application Ser. No. 13/394,091 entitled "Tracking the Probability for Imminent Hypoglycemia in Diabetes from Self-Monitoring Blood Glucose (SMBG) Data," filed Mar. 2, 2012; U.S. Patent Application Publication No. 2012/0191361, Jul. 26, 2012. (01681-10)

h. International Patent Application No. PCT/US2010/047711 entitled "Tracking the Probability for Imminent Hypoglycemia in Diabetes from Self-Monitoring Blood Glucose (SMBG) Data," filed Sep. 2, 2010. (01681-02)

i. U.S. patent application Ser. No. 13/380,839 entitled "System, Method, and Computer Simulation Environment for In-silico Trials in Pre-Diabetes and Type 2 Diabetes," filed Feb. 10, 2012; U.S. Patent Application Publication No. 2012/0130698, May 24, 2012. (01666-03)

j. International Patent Application No. PCT/US2010/040097 entitled "System, Method, and Computer Simulation Environment for In-silico Trials in Prediabetes and Type 2 Diabetes," filed Jun. 25, 2010. (01666-02)

k. U.S. patent application Ser. No. 13/322,943 entitled "System Coordinator and Modular Architecture for Open-Loop and Closed-Loop Control of Diabetes," filed Nov. 29, 2011; U.S. Patent Application Publication No. 2012/0078067, Mar. 29, 2012. (01660-03)

l. International Patent Application No. PCT/US2010/036629 entitled "System Coordinator and Modular Architecture for Open-Loop and Closed-Loop Control of Diabetes," filed May 28, 2010. (01660-02)

m. U.S. patent application Ser. No. 13/203,469 entitled "CGM-Based Prevention of Hypoglycemia via Hypoglycemia Risk Assessment and Smooth Reduction Insulin Delivery," filed Oct. 3, 2011; U.S. Patent Application Publication No. 2012/0059353, Mar. 8, 2012. (01637-09)

n. International Patent Application No. PCT/US2010/025405 entitled "CGM-Based Prevention of Hypoglycemia via Hypoglycemia Risk Assessment and Smooth Reduction Insulin Delivery," filed Feb. 25, 2010. (01637-04)

o. U.S. patent application Ser. No. 13/131,467 entitled "Method, System, and Computer Program Product for Tracking of Blood Glucose Variability in Diabetes," filed May 26, 2011; U.S. Patent Application Publication No. 2011/0264378, Oct. 27, 2011. (01616-08)

p. International Patent Application No. PCT/US2009/065725 entitled "Method, System, and Computer Program Product for Tracking of Blood Glucose Variability in Diabetes," filed Nov. 24, 2009. (01616-03)

q. U.S. application Ser. No. 12/740,275, entitled "PREDICTIVE CONTROL BASED SYSTEM AND METHOD FOR CONTROL OF INSULIN DELIVERY IN DIABETES USING GLUCOSE SENSING", filed Apr. 28, 2010;

r. International Patent Application Serial No. PCT/US2008/082063, entitled "Model Predictive Control Based Method for Closed-Loop Control of Insulin Delivery in Diabetes Using Continuous Glucose Sensing", filed Oct. 31, 2008;

s. U.S. patent application Ser. No. 12/975,580 entitled "Method, System, and Computer Program Product for the Evaluation of Glycemic Control in Diabetes from Self-Monitoring Data," filed Dec. 22, 2010; U.S. Patent Application Publication No. 2012/0004512, Jan. 5, 2012. (00543-34)

t. U.S. patent application Ser. No. 11/305,946 entitled "Method, System, and Computer Program Product for the Evaluation of Glycemic Control in Diabetes from Self-Monitoring Data," filed Dec. 19, 2005; U.S. Pat. No. 7,874,985, issued Jan. 25, 2011. (00543-30)

u. U.S. patent application Ser. No. 10/240,228 entitled "Method, System, and Computer Program Product for the Evaluation of Glycemic Control in Diabetes from Self-Monitoring Data," filed Sep. 26, 2002; U.S. Pat. No. 7,025,425, issued Apr. 11, 2006. (00543-19)

v. International Patent Application No. PCT/US2001/009884 entitled "Method, System, and Computer Program Product for the Evaluation of Glycemic Control in Diabetes," filed Mar. 29, 2001. (00543-02)

w. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data," filed Dec. 17, 2009; U.S. Patent Application Publication No. 2010/0198520, Aug. 5, 2010. (01411-10)

x International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data," filed Jul. 8, 2008. (01411-02)

y. U.S. patent application Ser. No. 12/664,444 entitled "Method, System and Computer Simulation Environment for Testing of Monitoring and Control Strategies in Diabetes," filed Dec. 14, 2009; U.S. Patent Application Publication No. 2010/0179768, Jul. 15, 2010. (01420-04)

z. International Patent Application No. PCT/US2008/067725 entitled "Method, System and Computer Simulation Environment for Testing of Monitoring and Control Strategies in Diabetes," filed Jun. 20, 2008. (01420-03)

aa. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes," filed May 22, 2009; U.S. Patent Application Publication No. 2010/0057043, Mar. 4, 2010. (01336-05)

bb. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes," filed Nov. 27, 2007. (01336-04)

cc. U.S. patent application Ser. No. 12/065,257 entitled "Accuracy of Continuous Glucose Sensors," filed Aug. 29, 2008; U.S. Patent Application Publication No. 2008/0314395, Dec. 25, 2008. (01172-07)

dd. International Patent Application No. US2006/033724 entitled "Method for Improvising Accuracy of Continuous Glucose Sensors and a Continuous Glucose Sensor Using the Same," filed Aug. 29, 2006. (01172-02)

ee. U.S. patent application Ser. No. 12/159,891 entitled "Method, System and Computer Program Product for Evaluation of Blood Glucose Variability in Diabetes from Self-Monitoring Data," filed Jul. 2, 2008; U.S. Patent Application Publication No. 2009/0171589, Jul. 2, 2009. (01221-11)

ff. International Patent Application No. PCT/US2007/000370 entitled "Method, System and Computer Program Product for Evaluation of Blood Glucose Variability in Diabetes from Self-Monitoring Data," filed Jan. 5, 2007. (01221-03)

gg. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes," filed Nov. 20, 2007; U.S. Patent Application Publication No. 2008/0154513, Jun. 26, 2008. (01342-02)

hh. International Patent Application No. PCT/US2007/082744 entitled "Method, System and Computer Program Product for Real-Time Detection of Sensitivity Decline in Analyte Sensors," filed Oct. 26, 2007. (01312-03)

ii. U.S. patent application Ser. No. 11/925,689 entitled "Method, System and Computer Program Product for Real-Time Detection of Sensitivity Decline in Analyte Sensors," filed Oct. 26, 2007; U.S. Pat. No. 8,135,548, issued Mar. 13, 2012. (01312-02)

jj. U.S. patent application Ser. No. 11/578,831 entitled "Method, System and Computer Program Product for Evaluating the Accuracy of Blood Glucose Monitoring Sensors/Devices," filed Oct. 18, 2006; U.S. Pat. No. 7,815,569, issued Oct. 19, 2010. (00986-03)

kk. International Patent Application No. US2005/013792 entitled "Method, System and Computer Program Product for Evaluating the Accuracy of Blood Glucose Monitoring Sensors/Devices," filed Apr. 21, 2005. (00986-02)

ll. U.S. patent application Ser. No. 10/592,883 entitled "Method, Apparatus, and Computer Program Product for Stochastic Psycho-physiological Assessment of Attentional Impairments," filed Sep. 15, 2006; U.S. Pat. No. 7,761,144, issued Jul. 20, 2010. (00554-11)

mm. International Patent Application No. US2005/008908 entitled "Method, Apparatus, and Computer Program Product for Stochastic Psycho-physiological Assessment of Attentional Impairments," filed Mar. 17, 2005. (00554-10)

nn. U.S. patent application Ser. No. 10/524,094 entitled "Method, System, And Computer Program Product For The Processing Of Self-Monitoring Blood Glucose (SMBG) Data To Enhance Diabetic Self-Management," filed Feb. 9, 2005. (00543-22)

ss. International Patent Application No. PCT/US2003/025053 entitled "Managing and Processing Self-Monitoring Blood Glucose," filed Aug. 8, 2003. (00543-21)

What is claimed is:

1. An electronic system that simulates a glucose-insulin metabolic system of a T1DM subject, comprising:
   an electronic subsystem configured to model dynamic glucose concentration in the T1DM subject, including
     an electronic module configured to model glucagon action on endogenous glucose production (EGP(t)),
     an electronic module configured to model meal glucose rate of appearance (Ra(t)),
     an electronic module configured to model insulin-dependent glucose utilization ($U_{id}(t)$), according to following equation:

$$U_{id}(t) = \frac{[V_{m0} + V_{mx} \cdot X(t) \cdot (1 + r_1 \cdot \text{risk})] \cdot G_t(t)}{K_{m0} + G_t(t)}$$

where $G_t(t)$ is an amount of glucose in tissue, X(t) is insulin action on glucose utilization and $[V_{m0}, V_{mx}, K_{m0}, p_{2U}]$ are model parameters, where $V_{m0}$ governs amplitude of insulin action on glucuose utilization at basal steady state, $V_{mx}$ governs amplitude of insulin action on glucuose utilization, $K_{m0}$ governs glucose control on glucose utilization, $p_{2U}$ accounts for delay between insulin signal and insulin action on glucose utilization, and $$\text{risk} = \begin{cases} 0 & \text{if } G \geq G_b \\ 10 \cdot [f(G)]^2 & \text{if } G_{th} \leq G < G_b \\ 10 \cdot [f(G_{th})]^2 & \text{if } G < G_{th} \end{cases}$$

with G being total glucose, $G_b$ being patient basal glucose, $G_{th}$ a hypoglycemic threshold, which is set at 60 mg/dl, and risk is a measure of risk of hypoglycemia, $$f(G) = \log\left(\frac{G}{G_b}\right)^{r2}$$

and [r1, r2] are additional randomly generated integers;
   an electronic module configured to model renal excretion of glucose (E(t));
   a subsystem configured to model dynamic insulin concentration in said T1DM subject, including
     an electronic module configured to model insulin secretion (S(t));
     an electronic module configured to model glucagon subcutaneous transport;
   an electronic database containing a population of virtual T1DM subjects, each virtual subject having a plurality of metabolic parameters with values within a range of values derived from in vivo T1DM subjects; and
   a processing module configured to calculate an effect of variation of at least one metabolic parameter value on the glucose-insulin metabolic system of a virtual subject by inputting said plurality of metabolic parameter values including said at least one varied metabolic parameter value into said glucose concentration and insulin concentration subsystems;
   wherein calculated effects of variation of at least one metabolic parameter value are outputted by said processing module and used to determine effectiveness of insulin treatment strategies that vary said at least one metabolic parameter value on a subject.

2. The electronic system as set forth in claim 1, wherein said glucose concentration subsystem models T1DM glucose concentration G(t) in accordance with following equations:

$$\dot{X}(t) = -p_2 \cdot X(t) + p_2 \cdot SI \cdot [I(t) - I_b] \quad X(0) = 0$$

$$\dot{G}(t) = \begin{cases} -[SG + X(t) \cdot (1 + r_1 \cdot \text{risk})] \cdot \\ \quad G(t) + SG \cdot G_b + \frac{GIR(t)}{V} & \text{if } G(t) < G_b \\ -[SG + X(t)] \cdot \\ \quad G(t) + SG \cdot G_b + \frac{GIR(t)}{V} G(0) = Gb & \text{otherwise} \end{cases} \quad G(0) = G_b$$

where G(t) is plasma glucose concentration, I(t) plasma insulin concentration, GIR(t) is exogenous glucose infusion rate, SG, SI, p2, V, rI and r2 are model parameters.

3. The electronic system as set forth in claim 2, further comprising an electronic module that models glucagon secretion and kinetics in accordance with following equations:

$$\dot{Gn}(t) = -k_{OGn} \cdot Gn(t) + GSR(t) \quad Gn(0) = Gn_b$$

$$GSR(t) = Y_g(t) + k_{GSRd} \cdot \max\left(-\frac{dG(t)}{dt}, 0\right)$$

$$\dot{Y}_g(t) = -\alpha_g \cdot \left[Y_g - \max\left(\frac{k_{GSRs} \cdot [G_{Th} - G(t)]}{I(t) - I_{th} + 1} + GSR_b, 0\right)\right]$$

$$Y_g(0) = GSR_b$$

where Gn(t) is a plasma glucagon concentration, GSR(t) is a glucagon secretion, $GSR_b$ is its basal value, $k_{OGn}$ is glucagon clearance rate, G(t) is plasma glucose and I(t) is plasma insulin concentration, $G_{Th}$ is a glucose threshold, $I_{th}$ is a threshold above which plasma insulin inhibits glucagon secretion, dG(t)/dt is a glucose rate of change, $k_{GSRs}$ is an alpha-cell responsivity to glucose level, 1/αg is a delay between static glucagon secretion and plasma glucose, and $k_{GSRd}$ is the alpha-cell responsivity to the glucose rate of change.

4. The electronic system as set forth in claim 2, wherein said electronic module that models glucagon action on endogenous glucose production implements said model of glucagon action on endogenous glucose production in accordance with following equations:

$$EGP(t) = k_{p1} - k_{p2} \cdot G_p(t) - k_{p3} \cdot X^L(t) + k_{counter} \cdot XGn(t)$$

$$\dot{I}'(t) = -k_i \cdot [I'(t) - I(t)] I'(0) = 0$$

$$\dot{X}^L(t) = -k_i \cdot [X^L(t) - I'(t)] X^L(0) = 0$$

$$\dot{X}Gn(t) = -k_{XGn} \cdot XGn(t) + k_{XGn} \cdot \max[(Gn(t) - Gn_b), 0] XGn(0) = 0$$

where EGP(t) is endogenous glucose production, $G_p(t)$ is glucose amount in a plasma compartment, $X^L(t)$ is a delayed insulin action in the liver of a subject, XGn(t) is a delayed glucagon action on EGP, Gn(t) is plasma glucagon concentration and $k_i$, $k_{p1}$, $k_{p2}$, $k_{p3}$, $k_{counter}$ and $k_{XGn}$ are model parameters.

5. The electronic system as set forth in claim 1, wherein said electronic module that models glucagon subcutaneous transport implements said model of glucagon subcutaneous transport in accordance with following equations:

$$\dot{x}_1(t) = -\left(k_1 + k_2 \frac{(x_1(t)/k_3)^{k_4}}{1+(x_1(t)/k_3)^{k_4}}\right)x_1(t) - k_6 x_1(t)$$

$$\dot{x}_2(t) = \left(k_1 + k_2 \frac{(x_1(t)/k_3)^{k_4}}{1+(x_1(t)/k_3)^{k_4}}\right)x_1(t) - k_5 x_2(t)$$

$$\dot{x}_3(t) = k_5 x_2(t) - k_7 x_3(t)$$

where $x_3$ is the plasma glucagon concentration and both $x_1$ and $x_2$ are subcutaneous compartments, $k_5$ and $k_6$ correspond to degradation of glucagon in subcutaneous tissues, $k_1$-$k_4$ describe a nonlinear transport in the subcutaneous tissues, and $k_7$ corresponds to plasma clearance.

6. The electronic system as set forth in claim 5, wherein glucagon transport model parameters are as follows:

| parameters | μ | σ |
|---|---|---|
| $k_1$ | −5.3877 | 1.6259 |
| $k_2$ | −3.9327 | 1.3582 |
| $k_3$ | fixed at $5 \cdot 10^{-3}$ | |
| $k_4$ | fixed at 3.5 | |
| $k_5$ | −3.364 | 1.277 |
| $k_6$ | −1.1883 | 1.1558 | wherein μ and σ are lognormal distributions.

7. The electronic system as set forth in claim 1, wherein said population of virtual subjects in said database meet the following criteria:
CR≤30 g/U
Mahalanobis distance lower than that corresponding to the 95% percentile
kmax>kmin
kmin>0.008
b<1
where CR is carbohydrate ratio.

8. The electronic system as set forth in claim 1, wherein said subsystems and modules are implemented as computer executable software stored on a non-transitory computer-readable storage medium and loaded into an electronic programmable computer.

9. The electronic system as set forth in claim 1, wherein said subsystems and modules are implemented as application specific integrated circuit modules.

10. A computer-executable program product embodied as computer executable code in a non-transitory computer-readable storage medium, wherein said computer-executable code when executed causes at least one processor to simulate a glucose-insulin metabolic system of a T2DM or prediabetic subject, said computer-executable code comprising:
subsystem code that models dynamic glucose concentration in a T1DM subject, including an electronic module that models glucagon action on endogenous glucose production (EGP(t)),
an electronic code module that models meal glucose rate of appearance (Ra(t)),
an electronic code module that models insulin-dependent glucose utilization ($U_{id}(t)$), according to following equation:

$$U_{id}(t) = \frac{[V_{m0} + V_{mx} \cdot X(t) \cdot (1 + r_1 \cdot \text{risk})] \cdot G_t(t)}{K_{m0} + G_t(t)}$$

where $G_t(t)$ is an amount of glucose in the tissue, X(t) is insulin action on glucose utilization and [$V_{m0}$, $V_{mx}$, $K_{m0}$, $p_{2U}$] are model parameters, where $V_{m0}$ governs amplitude of insulin action on glucuose utilization at basal steady state, $V_{mx}$ governs amplitude of insulin action on glucuose utilization, $K_{m0}$ governs glucose control on glucose utilization, $p_{2U}$ accounts for delay between insulin signal and insulin action on glucose utilization, and $$\text{risk} = \begin{cases} 0 & \text{if } G \geq G_b \\ 10 \cdot [f(G)]^2 & \text{if } G_{th} \leq G < G_b \\ 10 \cdot [f(G_{th})]^2 & \text{if } G < G_{th} \end{cases}$$

with G being total glucose, $G_b$ being patient basal glucose, $G_{th}$ is a hypoglycemic threshold, which is set at 60 mg/dl, and risk is a measure of risk of hypoglycemia, $$f(G) = \log\left(\frac{G}{G_b}\right)^{r_2}$$

and [r1, r2] are additional randomly generated integers;
an electronic code module that models renal excretion of glucose (E(t));
subsystem code that models dynamic insulin concentration in said T1DM subject, including
an electronic code module that models insulin secretion (S(t));
an electronic code module that models glucagon subcutaneous transport;
an electronic database containing a population of virtual T1DM subjects, each virtual subject having a plurality of metabolic parameters with values within a range of values derived from in vivo T1DM subjects; and
a calculating electronic code module that calculates an effect of variation of at least one metabolic parameter value on the glucose-insulin metabolic system of a virtual subject by inputting said plurality of metabolic parameter values including said at least one varied metabolic parameter value into said glucose concentration and insulin concentration subsystems:
wherein calculated effects of variation of at least one metabolic parameter value are outputted by said calculating electronic code module and used to determine effectiveness of insulin treatment strategies that vary said at least one metabolic parameter value on a subject.

11. The computer-executable program product as set forth in claim 10, wherein said glucose concentration subsystem models T1DM glucose concentration G(t) in accordance with following equations:

$$\dot{X}(t) = -p_2 \cdot X(t) + p_2 \cdot SI \cdot [I(t) - I_b] \quad X(0) = 0$$

$$\dot{G}(t) = \begin{cases} -[SG + X(t) \cdot (1 + r_1 \cdot \text{risk})] \cdot \\ G(t) + SG \cdot G_b + \dfrac{GIR(t)}{V} & \text{if } G(t) < G_b \\ -[SG + X(t)] \cdot \\ G(t) + SG \cdot Gb + \dfrac{GIR(t)}{V} G(0) = Gb & \text{otherwise} \end{cases} \quad G(0) = G_b$$

where G(t) is plasma glucose concentration, I(t) plasma insulin concentration, GIR(t) is exogenous glucose infusion rate, SG, SI, p2, V, r1 and r2 are model parameters.

12. The computer-executable program product as set forth in claim 11, further comprising an electronic code module that models glucagon secretion and kinetics in accordance with following equations:

$$\dot{Gn}(t) = -k_{OGn} \cdot Gn(t) + GSR(t) \quad Gn(0) = Gn_b$$

$$GSR(t) = Y_g(t) + k_{GSRd} \cdot \max\left(-\dfrac{dG(t)}{dt}, 0\right)$$

$$\dot{Y}_g(t) = -\alpha_g \cdot \left[Y_g - \max\left(\dfrac{k_{GSRs} \cdot [G_{Th} - G(t)]}{I(t) - I_{th} + 1} + GSR_b, 0\right)\right]$$

$$Y_g(0) = GSR_b$$

where Gn(t) is plasma glucagon concentration, GSR(t) is glucagon secretion, $GSR_b$ is its basal value, $k_{OGn}$ is glucagon clearance rate, G(t) is plasma glucose and I(t) is plasma insulin concentration, $G_{Th}$ is a glucose threshold, $I_{th}$ is a threshold above which plasma insulin inhibits glucagon secretion, dG(t)/dt is a glucose rate of change, $k_{GSRs}$ is an alpha-cell responsivity to glucose level, $1/\alpha g$ is a delay between static glucagon secretion and plasma glucose, and $k_{GSRd}$ is alpha-cell responsivity to the glucose rate of change.

13. The computer-executable program product as set forth in claim 10, wherein said electronic code module that models glucagon action on endogenous glucose production implements said model of glucagon action on endogenous glucose production in accordance with following equations:

$$EGP(t) = k_{p1} - k_{p2} \cdot G_p(t) - k_{p3} \cdot X^L(t) + k_{counter} \cdot XGn(t)$$

$$\dot{I}'(t) = -k_i \cdot [I'(t) - I(t)] I'(0) = 0$$

$$\dot{X}^L(t) = -k_i \cdot [X^L(t) - I'(t)] X^L(0) = 0$$

$$\dot{XGn}(t) = -k_{XGn} \cdot XGn(t) + k_{XGn} \cdot \max[(Gn(t) - Gn_b), 0] XGn(0) = 0$$

where EGP(t) is endogenous glucose production, $G_p(t)$ is glucose amount in a plasma compartment, $X^L(t)$ is a delayed insulin action in the liver of a subject, XGn(t) is a delayed glucagon action on EGP, Gn(t) is plasma glucagon concentration and $k_i$, $k_{p1}$, $k_{p2}$, $k_{p3}$, $k_{counter}$ and $k_{XGn}$ are model parameters.

14. The computer-executable program product as set forth in claim 10, wherein said electronic code module that models glucagon subcutaneous transport implements said model of glucagon subcutaneous transport in accordance with following equations:

$$\dot{x}_1(t) = -\left(k_1 + k_2 \dfrac{(x_1(t)/k_3)^{k_4}}{1 + (x_1(t)/k_3)^{k_4}}\right) x_1(t) - k_6 x_1(t)$$

$$\dot{x}_2(t) = \left(k_1 + k_2 \dfrac{(x_1(t)/k_3)^{k_4}}{1 + (x_1(t)/k_3)^{k_4}}\right) x_1(t) - k_5 x_2(t)$$

$$\dot{x}_3(t) = k_5 x_2(t) - k_7 x_3(t)$$

where $x_3$ is the plasma glucagon concentration and both $x_1$ and $x_2$ are subcutaneous compartments, $k_5$ and $k_6$ correspond to degradation of glucagon in subcutaneous tissues, $k_1$-$k_4$ describe a nonlinear transport in the subcutaneous tissues, and $k_7$ corresponds to the plasma clearance.

15. The computer-executable program product as set forth in claim 14, wherein glucagon transport model parameters are as follows:

| parameters | μ | σ |
|---|---|---|
| $k_1$ | −5.3877 | 1.6259 |
| $k_2$ | −3.9327 | 1.3582 |
| $k_3$ | fixed at 5 · 10$^{-3}$ | |
| $k_4$ | fixed at 3.5 | |
| $k_5$ | −3.364 | 1.277 |
| $k_6$ | −1.1883 | 1.1558 | wherein μ and σ are lognormal distributions.

16. The computer-executable program product as set forth in claim 10, wherein said population of virtual subjects in said database meet the following criteria:
CR≤30 g/U
Mahalanobis distance lower than that corresponding to the 95% percentile
kmax>kmin
kmin>0.008
b<1
where CR is carbohydrate ratio.

\* \* \* \* \*